(12) United States Patent
Davis et al.

(10) Patent No.: US 12,281,085 B2
(45) Date of Patent: Apr. 22, 2025

(54) BISFLUOROALKYL-1,4-BENZODIAZEPINONE COMPOUNDS AND METHODS OF USE THEREOF

(71) Applicants: Ayala Pharmaceuticals Inc., Wilmington, DE (US); Bristol-Myers Squibb Company, Princeton, NJ (US)

(72) Inventors: Matti Davis, Modiin (IL); Bruce S. Fischer, East Brunswick, NJ (US); Gaurav Bajaj, Plainsboro, NJ (US)

(73) Assignees: Immunome, Inc., Bothell, WA (US); Bristol-Myers Squibb Company, Princeton, NJ (US)

( * ) Notice: Subject to any disclaimer, the term of this patent is extended or adjusted under 35 U.S.C. 154(b) by 452 days.

(21) Appl. No.: 17/077,857

(22) Filed: Oct. 22, 2020

(65) Prior Publication Data

US 2021/0040050 A1 Feb. 11, 2021

Related U.S. Application Data

(63) Continuation-in-part of application No. PCT/US2019/030771, filed on May 5, 2019.

(60) Provisional application No. 62/667,540, filed on May 6, 2018.

(51) Int. Cl.
| | | |
|---|---|---|
| C07D 243/14 | (2006.01) | |
| A61K 9/00 | (2006.01) | |
| A61K 31/203 | (2006.01) | |
| A61K 31/44 | (2006.01) | |
| A61K 31/5513 | (2006.01) | |
| A61K 31/635 | (2006.01) | |
| A61K 39/395 | (2006.01) | |
| A61P 35/00 | (2006.01) | |

(52) U.S. Cl.
CPC .......... *C07D 243/14* (2013.01); *A61K 9/0019* (2013.01); *A61K 9/0053* (2013.01); *A61K 31/203* (2013.01); *A61K 31/44* (2013.01); *A61K 31/5513* (2013.01); *A61K 31/635* (2013.01); *A61K 39/3955* (2013.01); *A61P 35/00* (2018.01)

(58) Field of Classification Search
CPC .. C07D 243/14; A61K 9/0019; A61K 9/0053; A61K 31/203; A61K 31/44; A61K 31/5513; A61K 31/635; A61K 39/3955; A61K 31/436; A61K 45/06; A61K 31/675; A61K 33/243; A61K 2300/00; A61P 35/00; A61P 35/02
See application file for complete search history.

(56) References Cited

U.S. PATENT DOCUMENTS

| | | | | |
|---|---|---|---|---|
| 8,629,136 B2 * | 1/2014 | Gavai | ............... | A61K 31/5513 |
| | | | | 540/509 |
| 9,273,014 B2 | 3/2016 | Gavai et al. | | |
| 9,273,075 B2 * | 3/2016 | Gavai | ................... | A61K 45/06 |

FOREIGN PATENT DOCUMENTS

| | | | | |
|---|---|---|---|---|
| JP | 2017502933 A | 2/2018 | | |
| WO | WO-2010075074 A1 * | 7/2010 | .......... | C07D 401/14 |
| WO | WO-2012129353 A1 | 9/2012 | | |
| WO | WO-2013016081 A1 * | 1/2013 | ............. | A61P 35/00 |
| WO | WO-2013192274 A2 | 12/2013 | | |
| WO | WO-2014047372 A1 | 3/2014 | | |
| WO | WO-2014047391 A1 | 3/2014 | | |
| WO | WO-2014165718 A1 | 10/2014 | | |
| WO | WO-2017157825 A1 | 9/2017 | | |
| WO | WO-2017180389 A1 * | 10/2017 | .......... | A61K 31/444 |
| WO | WO-2018045273 A2 | 3/2018 | | |
| WO | WO-2018151836 A1 | 8/2018 | | |
| WO | WO-2018201051 A1 | 11/2018 | | |
| WO | WO-2018201056 A1 | 11/2018 | | |
| WO | WO-2019094626 A1 | 5/2019 | | |

OTHER PUBLICATIONS

Even, C. et al. (2017). Notch pathway inhibition with LY3039478 in adenoid cystic carcinoma (ACC). *Journal of Clinical Oncology* 2017 35:15_suppl, 6024-6024.
Ferrarotto, R. et al. (2017). Activating NOTCH1 mutations define a distinct subgroup of patients with adenoid cystic carcinoma who have poor prognosis, propensity to bone and liver metastasis, and potential responsiveness to Notch1 inhibitors. *Journal of Clinical Oncology*, 35(3), 352.
Li, M. et al. (2010). Combined inhibition of Notch signaling and Bcl-2/Bcl-xL results in synergistic antimyeloma effect. *Molecular Cancer Therapeutics*, 9(12), 3200-3209.
Manigat, L. et al. (2015). DDEL-16: Synergistic Combination of an HDAC Inhibitor (HDACi) and a Notch Inhibitor Versus Glioblastoma and Melanoma Cells. *Neuro-Oncology*, 17(Suppl 5), v76.

(Continued)

*Primary Examiner* — Brenda L Coleman
*Assistant Examiner* — Luisalberto Gonzalez
(74) *Attorney, Agent, or Firm* — Goodwin Procter LLP

(57) ABSTRACT

The present invention provides compositions comprising bisfluoroalkyl-1,4-benzodiazepinone compounds, including compounds of Formula (I) or prodrugs thereof;

in combination with an additional cancer therapeutic agent, and methods of use thereof for treating diseases and disorders such as cancer.

10 Claims, 6 Drawing Sheets

(56) References Cited

OTHER PUBLICATIONS

Massard, C. et al. (2018). First-in-human study of LY3039478, an oral Notch signaling inhibitor in advanced or metastatic cancer. *Annals of Oncology*, 29(9), 1911-1917.

Mukherjee, N. et al. (2016). Combining a GSI and BCL-2 inhibitor to overcome melanoma's resistance to current treatments. *Oncotarget*, 7(51), 84594-84607.

Panaccione, A. et al. (2016). NOTCH1 and SOX10 are essential for proliferation and radiation resistance of cancer stem-like cells in adenoid cystic carcinoma. *Clinical Cancer Research*, 22(8), 2083-2095.

Rao, S. S. et al. (2009). Inhibition of NOTCH signaling by gamma secretase inhibitor engages the RB pathway and elicits cell cycle exit in T-cell acute lymphoblastic leukemia cells. *Cancer research*, 69(7), 3060-3068.

Sakakibara-Konishi, J. et al. (2017). Combined antitumor effect of γ-secretase inhibitor and ABT-737 in Notch-expressing non-small cell lung cancer. *International Journal of Clinical Oncology*, 22(2), 257-268.

Stoeck, A. et al. (2014). Discovery of Biomarkers Predictive of GSI Response in Triple-Negative Breast Cancer and Adenoid Cystic Carcinoma: Biomarkers Predictive of GSI Response in Solid Tumors. *Cancer Discovery*, 4(10), 1154-1167.

Tijeras-Raballand, A. et al. (2018). Abstract B144: LY3039478, a novel Notch inhibitor, potentiates the antitumor effects of sorafenib in hepatocellular carcinoma (HCC). *Molecular Cancer Therapeutics*, 17(1_Supplement), B144-B144.

Andersson, E. R. et al. (2014). Therapeutic modulation of Notch signalling—are we there yet?. *Nature Reviews Drug Discovery*, 13(5), 357-378.

Chae, Y. K. et al. (2015). Adenoid cystic carcinoma: current therapy and potential therapeutic advances based on genomic profiling. *Oncotarget*, 6(35), 37117.

clinicaltrials.gov Identifier: NCT01363817, (last updated Jun. 2, 2011). Study to Evaluate the Safety and Tolerability of Weekly Intravenous (IV) Doses of BMS-906024 in Subjects With Acute T-cell Lymphoblastic Leukemia or T-cell Lymphoblastic Lymphoma. Retrieved from URL: https://clinicaltrials.gov/ct2/show/NCT01363817.

clinicaltrials.gov Identifier: NCT01653470, (last updated Apr. 18, 2018). Study to Evaluate Safety & Tolerability of BMS-906024 in Combination With Chemotherapy & to Define DLTs & MTD of BMS-906024 in Combination With One of the Following Chemotherapy Regimens; Weekly Paclitaxel, 5FU+Irinotecan or Carboplatin+Paclitaxel in Subjects With Advanced / Metastatic Solid Tumors. Retrieved from URL: https://clinicaltrials.gov/ct2/show/study/NCT01653470.

Dinner, S. et al. (2016). Targeting the mTOR pathway in leukemia. *Journal of Cellular Biochemistry*, 117(8), 1745-1752.

Fung, E. N. et al. (2015). Utilizing internal standard responses to assess risk on reporting bioanalytical results from hemolyzed samples. *The AAPS Journal*, 17(5), 1168-1176.

Gavai, A. V. et al. (2015). Discovery of clinical candidate BMS-906024: a potent pan-notch inhibitor for the treatment of leukemia and solid tumors. *ACS Medicinal Chemistry Letters*, 6(5), 523-527.

Hill, T. et al. (Nov. 2017). Gamma secretase inhibition increases recognition of multiple myeloma by BCMA-specific chimeric antigen receptor modified T cells. In *Journal for Immunotherapy of Cancer* (vol. 5). Campus, 4 Crinan St, London N1 9xw, England: BMC.

International Preliminary Report on Patentability (Chapter I) dated Nov. 10, 2020, issued in the corresponding PCT International Application No. PCT/US2019/030771, dated May 5, 2019.

International Search Report dated Aug. 15, 2019, issued in the corresponding PCT International Application No. PCT/US2019/030771, dated May 5, 2019.

Morgan, K. M. et al. (2017). Gamma secretase inhibition by BMS-906024 enhances efficacy of paclitaxel in lung adenocarcinoma. *Molecular cancer therapeutics*, 16(12), 2759-2769.

Mur, E. B. et al. (2020). Notch inhibition overcomes resistance to tyrosine kinase inhibitors in EGFR-driven lung adenocarcinoma. *The Journal of Clinical Investigation*, 130(2), 612-624.

Siu, L. L. et al. (2019). METEOR-1: a phase I study of GSK3326595, a first-in-class protein arginine methyltransferase 5 (PRMT5) inhibitor, in advanced solid tumours. *Annals of Oncology*, 30, v159.

Sosa Iglesias, V. et al. (2018). Synergistic effects of NOTCH/γ-secretase inhibition and standard of care treatment modalities in non-small cell lung cancer cells. *Frontiers in Oncology*, 8, 460.

Tchekmedyian, V. et al. (2019). Phase II study of lenvatinib in patients with progressive, recurrent or metastatic adenoid cystic carcinoma. *Journal of Clinical Oncology*, 37(18), 1529.

Xie, J. et al. (2016). mTOR inhibitors in cancer therapy. *F1000Research*, 5.

Tijeras-Raballand, A. et al. (2018). Abstract B145: Addition of galunisertib to DC101 improved angiogenesis inhibition and tumor growth control in hepatocellular carcinoma (HCC). Molecular Cancer Therapeutics, 17(1_Supplement), B145-B145.

Ju, W. et al. (Jan. 2018). Abstract A171: Epigenetic modification of α-N-acetylgalactosaminidase (NAGA) enhances cisplatin resistance in ovarian cancer. *Molecular Cancer Therapeutics*, 17(1_Supplement), A171-A171.

Locati, L. D. et al. (2016). A phase II study of sorafenib in recurrent and/or metastatic salivary gland carcinomas: Translational analyses and clinical impact. *European Journal of Cancer*, 69, 158-165.

\* cited by examiner

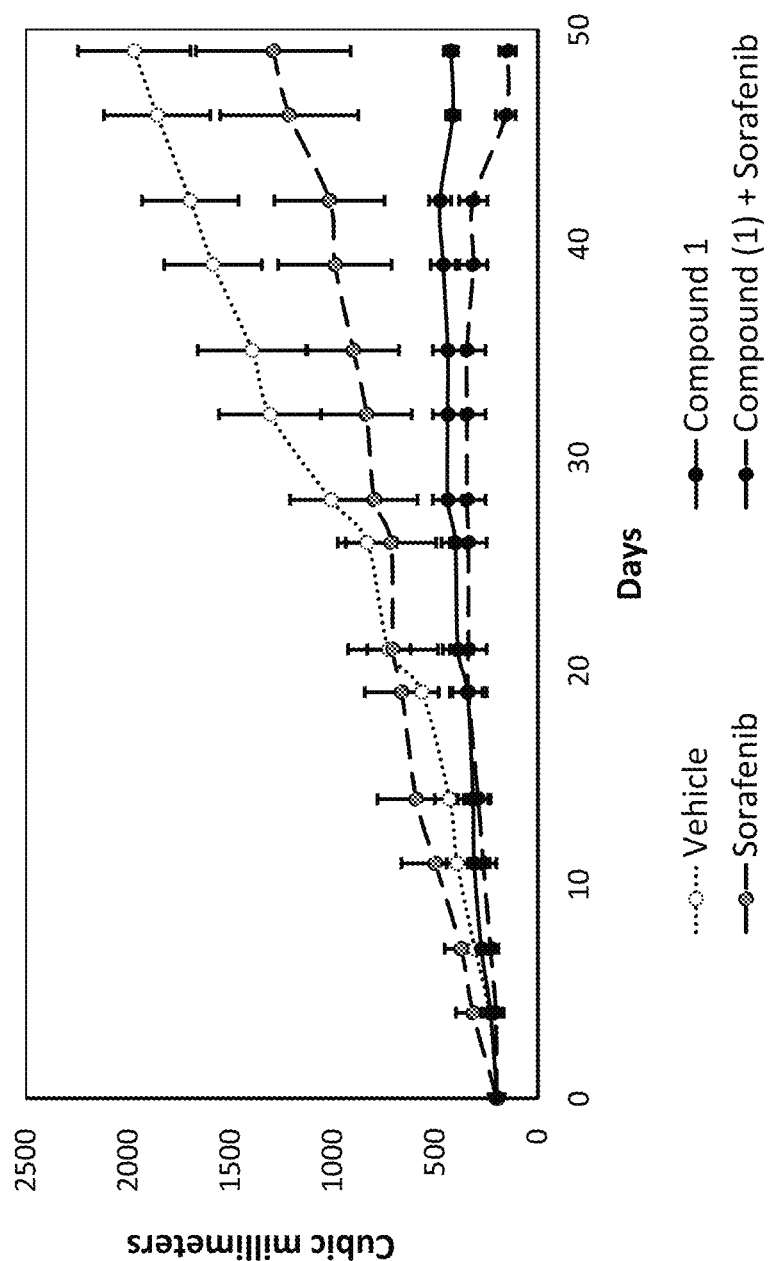

BISFLUOROALKYL-1,4-BENZODIAZEPINONE COMPOUNDS AND METHODS OF USE THEREOF

FIELD OF THE INVENTION

The present invention provides compositions comprising bisfluoroalkyl-1,4-benzodiazepinone compounds, including compounds of Formula (I) or prodrugs thereof;

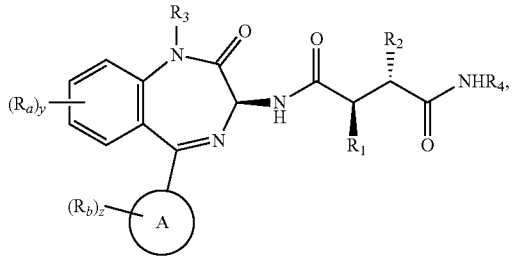

(I)

in combination with an additional cancer therapeutic agent, and methods of use thereof for treating diseases and disorders such as cancer.

BACKGROUND OF THE INVENTION

Benzodiazepinone compounds as Notch inhibitors useful for the treatment of conditions related to the Notch pathway, such as cancer and other proliferative diseases are known. Using a combination of benzodiazepinone compounds with other cancer therapeutics may enhance the efficacy of benzodiazepinone compounds for treating cancer.

SUMMARY OF THE INVENTION

The present invention provides a composition comprising one or more compounds represented by the structure of Formula (I):

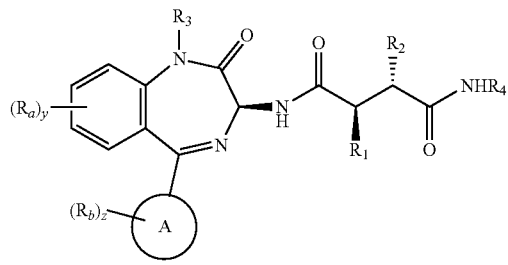

(I)

and/or at least one salt thereof, wherein:
R is —CH$_2$CF$_3$ or —CH$_2$CH$_2$CF$_3$;
R$_2$ is —CH$_2$CF$_3$, —CH$_2$CH$_2$CF$_3$, or —CH$_2$CH$_2$CH$_2$CF$_3$;
R$_3$ is H, —CH$_3$ or Rx;
R$_4$ is H or R$_y$;
R$_x$
is: —CH$_2$OC(O)CH(CH$_3$)NH$_2$, —CH$_2$OC(O)CH(NH$_2$)CH(CH$_3$)$_2$, —CH$_2$OC(O)CH((CH(C

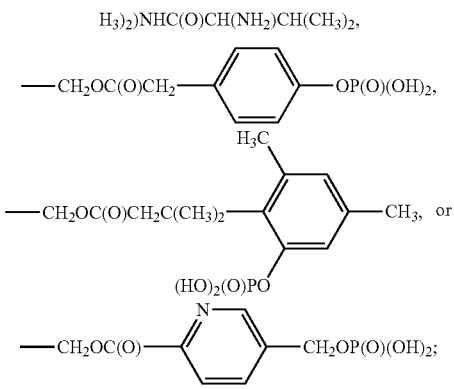

R$_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;
Ring A is phenyl or pyridinyl;
each R$_a$ is independently F, Cl, —CN, —OCH$_3$, C$_{1-3}$ alkyl, —CH$_2$OH, —CF$_3$, cyclopropyl, —OCH$_3$, —O(cyclopropyl) and/or —NHCH$_2$CH$_2$OCH$_3$;
each R$_b$ is independently F, Cl, —CH$_3$, —CH$_2$OH, —CF$_3$, cyclopropyl, and/or —OCH$_3$;
y is zero, 1 or 2; and
z is zero, 1, or 2
in combination with a composition comprising Venclexta, Sorafenib, a retinoic acid derivative, or a combination thereof.

The present invention also provides a method of treating, suppressing or inhibiting a proliferative disease in a subject comprising the step of administering to said subject a first composition comprising one or more compounds represented by the structure of Formula (I):

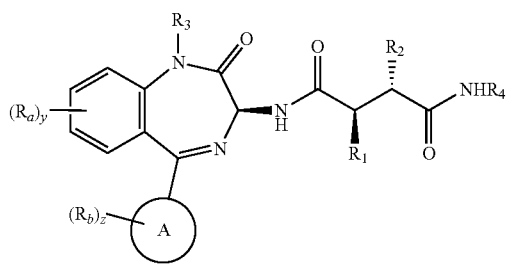

and/or at least one salt thereof, wherein:
R$_1$ is —CH$_2$CF$_3$ or —CH$_2$CH$_2$CF$_3$;
R$_2$ is —CH$_2$CF$_3$, —CH$_2$CH$_2$CF$_3$, or —CH$_2$CH$_2$CH$_2$CF$_3$;
R$_3$ is H, —CH$_3$ or Rx;
R$_4$ is H or R$_y$;
R$_x$
is: —CH$_2$OC(O)CH(CH$_3$)NH$_2$, —CH$_2$OC(O)CH(NH$_2$)CH(CH$_3$)$_2$, —CH$_2$OC(O)CH((CH(C

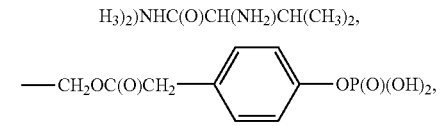

—CH₂OC(O)CH₂C(CH₃)₂—[3-methyl-5-phosphonophenyl with CH₃]—, or

—CH₂OC(O)—[pyridinyl]—CH₂OP(O)(OH)₂;

R_y is: —SCH₂CH(NH₂)C(O)OH, —SCH₂CH(NH₂)C(O)OCH₃, or —SCH₂CH(NH₂)C(O)OC(CH₃)₃;
Ring A is phenyl or pyridinyl;
each R_a is independently F, Cl, —CN, —OCH₃, $C_{1-3}$ alkyl, —CH₂OH, —CF₃, cyclopropyl, —OCH₃, —O(cyclopropyl) and/or —NHCH₂CH₂OCH₃;
each R_b is independently F, Cl, —CH₃, —CH₂OH, —CF₃, cyclopropyl, and/or —OCH₃;
y is zero, 1 or 2; and
z is zero, 1, or 2
and comprising the step of administering a second composition comprising Venclexta, Sorafenib, a retinoic acid derivative, or a combination thereof.

BRIEF DESCRIPTION OF THE DRAWINGS

FIG. 1D. Tumor volume (Mean+/−SEM) over time in ACC animal models administered Compound (1) alone, Sorafenib alone, or a combination of Compound (1)+Sorafenib.

DETAILED DESCRIPTION OF THE PRESENT INVENTION

Figure 1A:
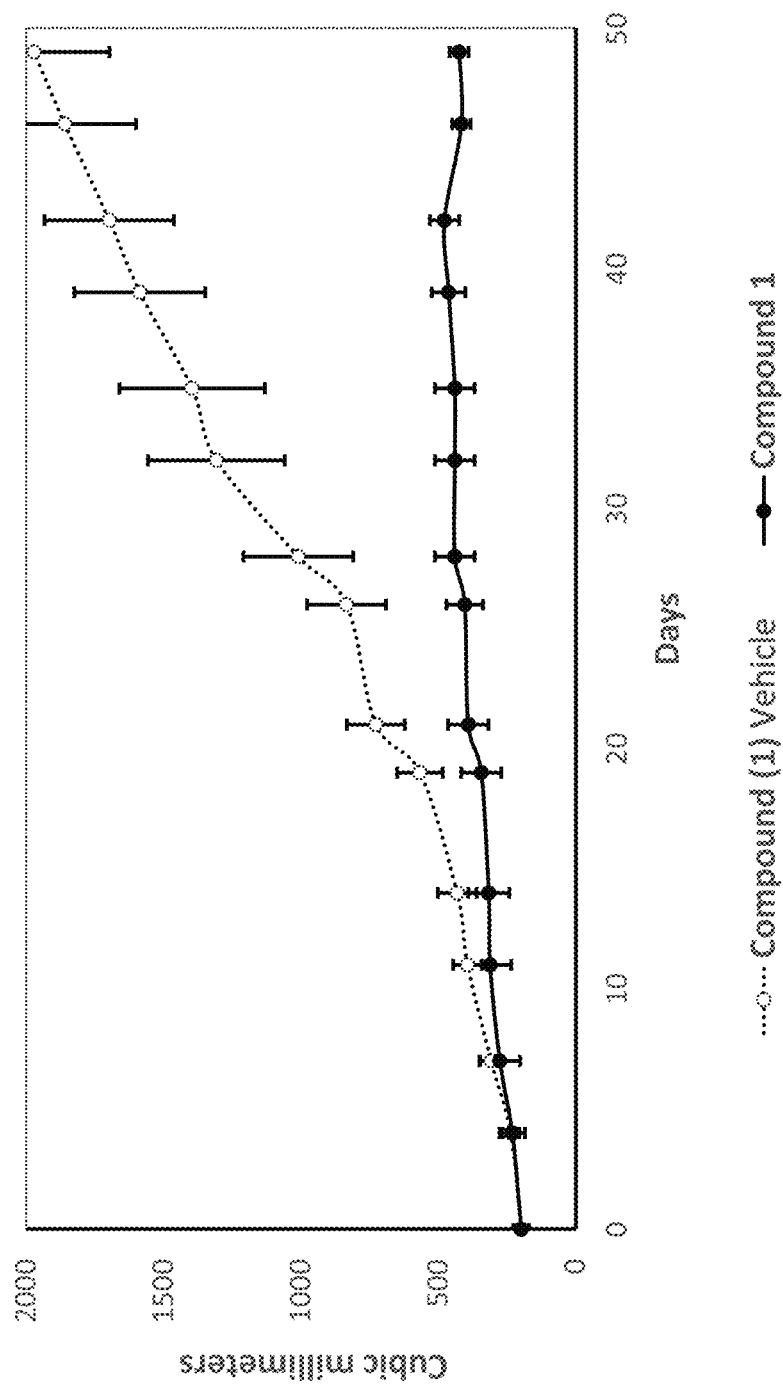
FIG. 1A. Tumor volume (Mean+/−SEM) over time in ACC animal models administered vehicle or Compound (1).

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, compositions of the present invention or for use in the methods of the present invention comprise one or more gamma secretase inhibitors. In one embodiment, the gamma secretase inhibitor comprises a bisfluoroalkyl-1,4-benzodiazepinone compound.

In one embodiment, compositions of the present invention or for use in the methods of the present invention comprise one or more Notch inhibitors. In one embodiment, the Notch inhibitor comprises a bisfluoroalkyl-1,4-benzodiazepinone compound.

Bisfluoroalkyl-1,4-benzodiazepinone Compounds

In one embodiment, the present invention provides compositions comprising compounds represented by the structure of Formula (I):

(I)

[Chemical structure of Formula (I): a benzodiazepinone with substituents $R_3$, $(R_a)_y$, $R_1$, $(R_b)_z$ on Ring A, linked to a succinamide with $R_2$ and NHR₄]

and/or at least one salt thereof, wherein:
$R_1$ is —CH₂CF₃ or —CH₂CH₂CF₃;
$R_2$ is —CH₂CF₃, —CH₂CH₂CF₃, or —CH₂CH₂CH₂CF₃;
$R_3$ is H, —CH₃ or Rx;
$R_4$ is H or $R_y$;
$R_x$ is: —CH₂OC(O)CH(CH₃)NH₂, —CH₂OC(O)CH(NH₂)CH(CH₃)₂, —CH₂OC(O)CH((C

H(CH₃)₂)NHC(O)CH(NH₂)CH(CH₃)₂,

—CH₂OC(O)CH₂—[phenyl]—OP(O)(OH)₂,

—CH₂OC(O)CH₂C(CH₃)₂—[3-methyl-5-phosphonophenyl with CH₃]—, or

—CH₂OC(O)—[pyridinyl]—CH₂OP(O)(OH)₂;

R_y is: —SCH₂CH(NH₂)C(O)OH, —SCH₂CH(NH₂)C(O)OCH₃, or —SCH₂CH(NH₂)C(O)OC(CH₃)₃;
Ring A is phenyl or pyridinyl;
each R_a is independently F, Cl, —CN, —OCH₃, $C_{1-3}$ alkyl, —CH₂OH, —CF₃, cyclopropyl, —OCH₃, —O(cyclopropyl) and/or —NHCH₂CH₂OCH₃;
each R_b is independently F, Cl, —CH₃, —CH₂OH, —CF₃, cyclopropyl, and/or —OCH₃;
y is zero, 1 or 2; and
z is zero, 1, or 2.

In one embodiment, the present invention provides compositions comprising compounds represented by the structure of Formula (II):

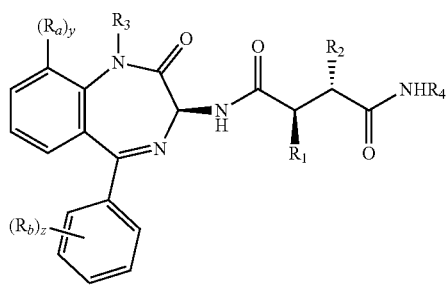

wherein R₃ is H or —CH₃; and y is zero or 1.

In one embodiment, the present invention provides compositions comprising compounds of Formula (III):

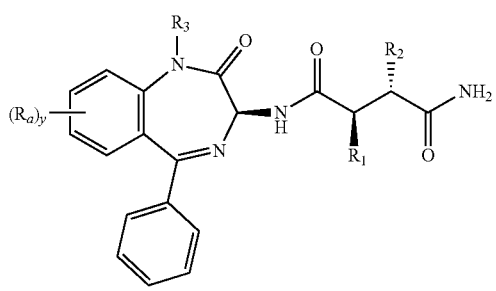

or prodrugs or salts thereof; wherein:
R₁ is —CH₂CF₃ or —CH₂CH₂CF₃;
R₂ is —CH₂CF₃, —CH₂CH₂CF₃, or —CH₂CH₂CH₂CF₃;
R₃ is H or —CH₃;
each R_a is independently F, Cl, —CN, —OCH₃, and/or —NHCH₂CH₂OCH₃; and
y is zero, 1, or 2.

In one embodiment, R₂ is —CH₂CF₃ or —CH₂CH₂CF₃. In one embodiment, R₁ is —CH₂CF₃ or —CH₂CH₂CF₃ and R₂ is —CH₂CF₃ or —CH₂CH₂CF₃. In another embodiment, R₁ is —CH₂CH₂CF₃ and R₂ is —CH₂CH₂CF₃. In one embodiment, y is zero or 1. In another embodiment, y is 1 or 2. In another embodiment, y is 1 or 2.

The present invention also provides a method of treating, suppressing or inhibiting a proliferative disease in a subject comprising the step of administering to said subject a first composition comprising one or more compounds represented by the structure of Formula (I):

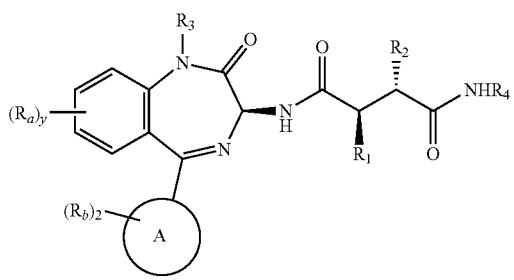

In another embodiment, the compound of Formula (III) comprises: (2R,3S)—N-((3S)-2-oxo-5-phenyl-2,3-dihydro-1H-1,4-benzodiazepin-3-yl)-2,3-bis(3,3,3-trifluoropropyl)succinamide (2)

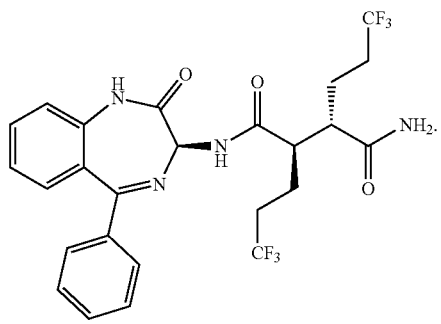 [SMILES: NC(=O)[C@@H](CCC(F)(F)F)[C@@H](CCC(F)(F)F)C(=O)N[C@H]1N=C(c2ccccc2)c2ccccc2NC1=O]

In another embodiment, the compound of Formula (III) comprises: (2R,3S)—N-((3S)-1-methyl-2-oxo-5-phenyl-2,3-dihydro-1H-1,4-benzodiazepin-3-yl)-2-(2,2,2-trifluoroethyl)-3-(3,3,3-trifluoropropyl)succinamide (3);

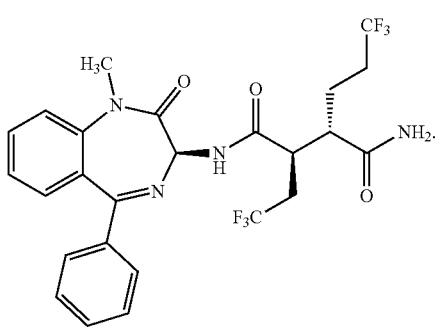

In another embodiment, the compound of Formula (III) comprises: (2R,3S)—N-((3S)-1-methyl-2-oxo-5-phenyl-2,3-dihydro-1H-1,4-benzodiazepin-3-yl)-3-(2,2,2-trifluoroethyl)-2-(3,3,3-trifluoropropyl)succinamide (4);

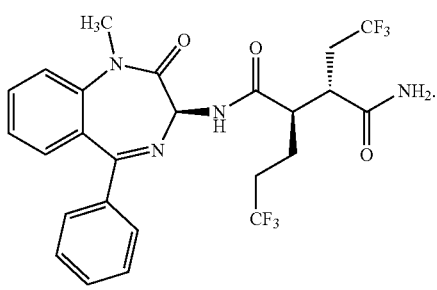

In another embodiment, the compound of Formula (III) comprises: (2R,3S)—N-((3S)-1-(²H₃)methyl-2-oxo-5-phenyl-2,3-dihydro-1H-1,4-benzodiazepin-3-yl)-2,3-bis(3,3,3-trifluoropropyl)succinamide (5);

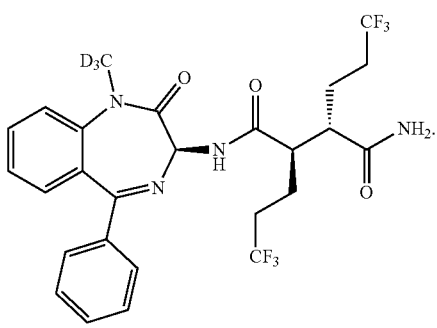

(5)

In another embodiment, the compound of Formula (III) comprises a compound of Formula (VI):

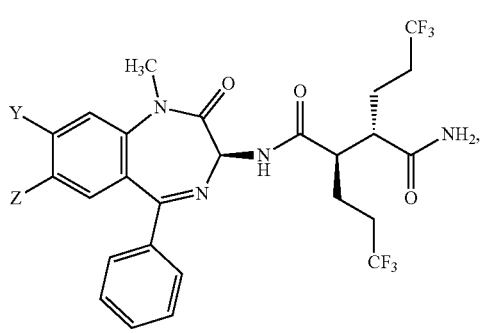

(VI)

which in one embodiment, comprises (2R,3S)—N-((3S)-7-chloro-1-methyl-2-oxo-5-phenyl-2,3-dihydro-1H-1,4-benzodiazepin-3-yl)-2,3-bis(3,3,3-trifluoropropyl)succinamide (6), i.e. Y═H and Z═Cl; (2R,3S)—N-((3S)-8-methoxy-1-methyl-2-oxo-5-phenyl-2,3-dihydro-1H-1,4-benzodiazepin-3-yl)-2,3-bis(3,3,3-trifluoropropyl)succinamide (7), i.e. Y═OCH₃ and Z═H; (2R,3S)—N-((3S)-8-fluoro-1l-methyl-2-oxo-5-phenyl-2,3-dihydro-1H-1,4-benzodiazepin-3-yl)-2,3-bis(3,3,3-trifluoropropyl)succinamide (8), i.e. Y═F and Z═H; (2R,3S)—N-((3S)-7-methoxy-1-methyl-2-oxo-5-phenyl-2,3-dihydro-1H-1,4-benzodiazepin-3-yl)-2,3-bis(3,3,3-trifluoropropyl)succinamide (9), Y═H and Z═OCH₃; (2R,3S)—N-((3S)-7-fluoro-1-methyl-2-oxo-5-phenyl-2,3-dihydro-1H-1,4-benzodiazepin-3-yl)-2,3-bis(3,3,3-trifluoropropyl)succinamide (10), i.e. Y═H and Z═F; or (2R,3S)—N-((3S)-8-chloro-1-methyl-2-oxo-5-phenyl-2,3-dihydro-1H-1,4-benzodiazepin-3-yl)-2,3-bis(3,3,3-trifluoropropyl)succinamide (11), i.e. Y═Cl and Z═H.

In another embodiment, the compound of Formula (III) comprises a compound of Formula (VII):

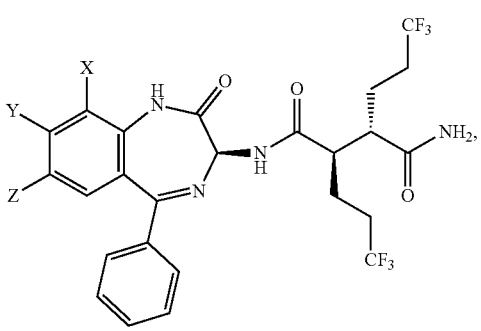

(VII)

which in one embodiment, comprises (2R,3S)—N-((3S)-9-methoxy-2-oxo-5-phenyl-2,3-dihydro-1H-1,4-benzodiazepin-3-yl)-2,3-bis(3,3,3-trifluoropropyl)succinamide (12), i.e. X═OCH₃, Y═H and Z═H; (2R,3S)—N-((3S)-8-methoxy-2-oxo-5-phenyl-2,3-dihydro-1H-1,4-benzodiazepin-3-yl)-2,3-bis(3,3,3-trifluoropropyl)succinamide (13), i.e. X═H, Y═OCH₃ and Z═H; (2R,3S)—N-((3S)-7-methoxy-2-oxo-5-phenyl-2,3-dihydro-1H-1,4-benzodiazepin-3-yl)-2,3-bis(3,3,3-trifluoropropyl)succinamide (14), i.e. X═H, Y═H and Z═OCH₃; (2R,3S)—N-((3S)-8-cyano-9-methoxy-2-oxo-5-phenyl-2,3-dihydro-1H-1,4-benzodiazepin-3-yl)-2,3-bis(3,3,3-trifluoropropyl)succinamide (15), i.e. X═OCH₃, Y═CN and Z═H; (2R,3S)—N-((3S)-8,9-dichloro-2-oxo-5-phenyl-2,3-dihydro-1H-1,4-benzodiazepin-3-yl)-2,3-bis(3,3,3-trifluoropropyl)succinamide (16), i.e. X═Cl, Y═Cl and Z═H; (2R,3S)—N-((3S)-9-fluoro-2-oxo-5-phenyl-2,3-dihydro-1H-1,4-benzodiazepin-3-yl)-2,3-bis(3,3,3-trifluoropropyl)succinamide (17), i.e. X═F, Y═H and Z═H; or (2R,3S)—N-((3S)-9-chloro-2-oxo-5-phenyl-2,3-dihydro-1H-1,4-benzodiazepin-3-yl)-2,3-bis(3,3,3-trifluoropropyl)succinamide (18), i.e. X═Cl, Y═H and Z═H.

In another embodiment, the compound of Formula (III) comprises: (2R,3S)—N-((3S)-2-oxo-5-phenyl-2,3-dihydro-1H-1,4-benzodiazepin-3-yl)-3-(4,4,4-trifluorobutyl)-2-(3,3,3-trifluoropropyl)succinamide (19);

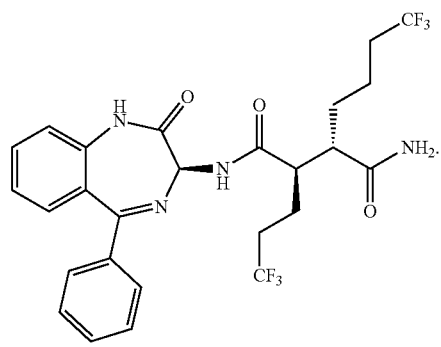

(19)

In another embodiment, the compound of Formula (III) comprises: (2R,3S)—N-((3S)-8-methoxy-2-oxo-5-phenyl-2,3-dihydro-1H-1,4-benzodiazepin-3-yl)-3-(4,4,4-trifluorobutyl)-2-(3,3,3-trifluoropropyl)succinamide (20)

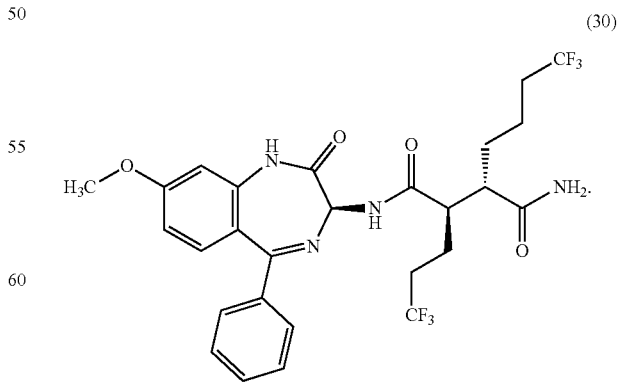

(30)

In another embodiment, the compound of Formula (III) comprises: (2R,3S)—N-((3S)-9-((2-methoxyethyl)amino)-

2-oxo-5-phenyl-2,3-dihydro-1H-1,4-benzodiazepin-3-yl)-2,3-bis(3,3,3-trifluoropropyl)succinamide (21)

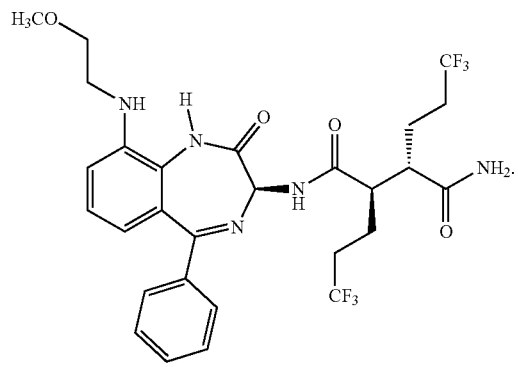

In another embodiment, the present invention provides compositions comprising compounds represented by the structure of Formula (I):

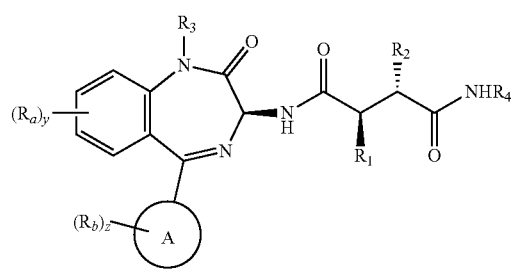

and/or at least one salt thereof, wherein:
R₁ is —CH₂CF₃;
R₂ is —CH₂CH₂CF₃, or —CH₂CH₂CH₂CF₃;
R₃ is H, —CH₃ or Rx;
R₄ is H or R$_y$;
R$_x$ is: —CH₂OC(O)CH(CH₃)NH₂, —CH₂OC(O)CH(NH₂)CH(CH₃)₂, —CH₂OC(O)CH((C

H(CH₃)₂)NHC(O)CH(NH₂)CH(CH₃)₂,

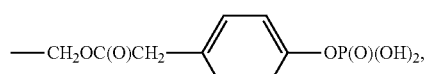

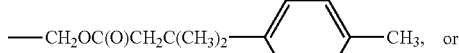

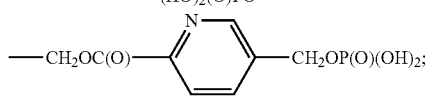

R$_y$ is: —SCH₂CH(NH₂)C(O)OH, —SCH₂CH(NH₂)C(O)OCH₃, or —SCH₂CH(NH₂)C(O)OC(CH₃)₃;

Ring A is phenyl or pyridinyl;
each R$_a$ is independently Cl, C₁₋₃ alkyl, —CH₂OH, —CF₃, cyclopropyl, —OCH₃, and/or —O(cyclopropyl);
each R$_b$ is independently F, Cl, —CH₃, —CH₂OH, —CF₃, cyclopropyl, and/or —OCH₃;
y is zero, 1 or 2; and
z is 1 or 2.

In another embodiment, Ring A is phenyl; and R₃ is H. In another embodiment, R₂ is —CH₂CH₂CF₃; and Ring A is phenyl. In another embodiment, R₂ is —CH₂CH₂CF₃; Ring A is phenyl; R$_a$ is C₁₋₃ alkyl or —CH₂OH; each R$_b$ is independently F and/or Cl; and y is 1.

In another embodiment, the present invention provides compositions comprising compounds represented by the structure of Formula (V):

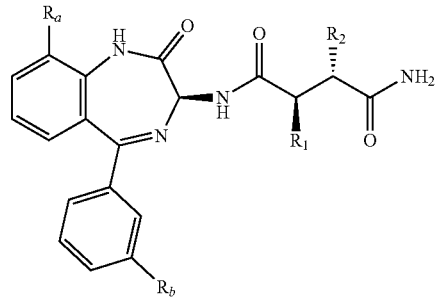

In another embodiment, the present invention provides compositions comprising compounds represented by the structure of Formula (V):

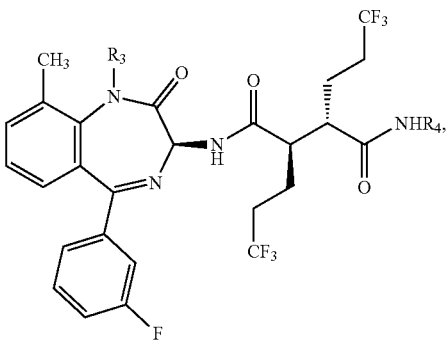

wherein R₃ is H or R.

In another embodiment, the present invention provides compositions comprising (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide (22); (2R,3S)—N-((3S)-5-(3-chlorophenyl)-9-ethyl-2-oxo-2,3-dihydro-1H-1,4-benzodiazepin-3-yl)-2,3-bis(3,3,3-trifluoropropyl)succinamide (23); (2R,3S)—N-((3S)-5-(3-chlorophenyl)-9-isopropyl-2-oxo-2,3-dihydro-1H-1,4-benzodiazepin-3-yl)-2,3-bis(3,3,3-trifluoropropyl)succinamide (24); (2R,3S)—N-(9-chloro-5-(3,4-dimethylphenyl)-2-oxo-2,3-dihydro-1H-1,4-benzodiazepin-3-yl)-3-(4,4,4-trifluorobutyl)-2-(3,3,3-trifluoropropyl)succinamide (25); (2R,3S)—N-(9-chloro-5-(3,5-dimethylphenyl)-2-oxo-2,3-dihydro-1H-1,4-benzodiazepin- 3-yl)-3-(4,4,4-trifluorobutyl)-2-(3,3,3-trifluoropropyl)succinamide (26); (2R,3S)—N-((3S)-9-ethyl-5-(3-methylphenyl)-2-oxo-2,3-dihydro-1H-1,4-benzodiazepin-3-yl)-2,3-bis(3,3,3-trifluoropropyl)succinamide (27); (2R,3S)—N-((3S)-5-(3-chlorophenyl)-9-methyl-2-oxo-2,3-dihydro-1H-1,4-benzodiazepin-3-yl)-2,3-bis(3,3,3-trifluoropropyl)succinamide (28); (2R,3S)—N-((3S)-5-(3-chlorophenyl)-9-methyl-2-oxo-2,3-dihydro-1H-1,4-benzodiazepin-3-yl)-3-(4,4,4-trifluorobutyl)-2-(3,3,3-trifluoropropyl)succinamide (29); (2R,3S)—N-((3S)-5-(3-methylphenyl)-2-oxo-9-(trifluoromethyl)-2,3-dihydro-1H-1,4-benzodiazepin-3-yl)-2,3-bis(3,3,3-trifluoropropyl)succinamide (30); (2R,3S)—N-((3S)-9-chloro-5-(3,5-dimethylphenyl)-2-oxo-2,3-dihydro-1H-1,4-benzodiazepin-3-yl)-2,3-bis(3,3,3-trifluoropropyl)succinamide (31); (2R,3S)—N-((3S)-5-(3-methylphenyl)-2-oxo-9-(trifluoromethyl)-2,3-dihydro-1H-1,4-benzodiazepin-3-yl)-3-(4,4,4-trifluorobutyl)-2-(3,3,3-trifluoropropyl)succinamide (32); (2R,3S)—N-((3S)-9-isopropyl-5-(3-methylphenyl)-2-oxo-2,3-dihydro-1H-1,4-benzodiazepin-3-yl)-2,3-bis(3,3,3-trifluoropropyl)succinamide (33); (2R,3S)—N-((3S)-9-(cyclopropyloxy)-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide (34); (2R,3S)—N-((3S)-9-(cyclopropyloxy)-5-(3-methylphenyl)-2-oxo-2,3-dihydro-1H-1,4-benzodiazepin-3-yl)-2,3-bis(3,3,3-trifluoropropyl)succinamide (35); (2R,3S)—N-((3S)-9-chloro-5-(3-methylphenyl)-2-oxo-2,3-dihydro-1H-1,4-benzodiazepin-3-yl)-3-(4,4,4-trifluorobutyl)-2-(3,3,3-trifluoropropyl) succinamide (36); (2R,3S)—N-((3S)-9-methyl-2-oxo-5-(3-(trifluoromethyl)phenyl)-2,3-dihydro-1H-1,4-benzodiazepin-3-yl)-3-(4,4,4-trifluorobutyl)-2-(3,3,3-trifluoropropyl) succinamide (37); (2R,3S)—N-((3S)-9-methyl-2-oxo-5-(3-(trifluoromethyl) phenyl)-2,3-dihydro-1H-1,4-benzodiazepin-3-yl)-2,3-bis(3,3,3-trifluoropropyl)succinamide (38); (2R,3S)—N-((3S)-9-chloro-5-(2-methylphenyl)-2-oxo-2,3-dihydro-1H-1,4-benzodiazepin-3-yl)-2,3-bis(3,3,3-trifluoropropyl)succinamide (39); (2R,3S)—N-((3S)-5-(4-fluorophenyl)-9-methyl-2-oxo-2,3-dihydro-1H-1,4-benzodiazepin-3-yl)-2,3-bis(3,3,3-trifluoropropyl) succinamide (40); (2R,3S)—N-((3S)-9-chloro-5-(3-cyclopropylphenyl)-2-oxo-2,3-dihydro-1H-1,4-benzodiazepin-3-yl)-2,3-bis(3,3,3-trifluoropropyl)succinamide (41); (2R,3S)—N-((3S)-5-(3-chlorophenyl)-9-methoxy-2-oxo-2,3-dihydro-1H-1,4-benzodiazepin-3-yl)-2,3-bis(3,3,3-trifluoropropyl)succinamide (42); (2R,3S)—N-((3S)-5-(4-chlorophenyl)-9-methoxy-2-oxo-2,3-dihydro-1H-1,4-benzodiazepin-3-yl)-2,3-bis(3,3,3-trifluoropropyl)succinamide (43); (2R,3S)—N-((3S)-9-chloro-5-(3-methylphenyl)-2-oxo-2,3-dihydro-1H-1,4-benzodiazepin-3-yl)-2,3-bis(3,3,3-trifluoropropyl)succinamide (44); (2R,3S)—N-((3S)-5-(3-methylphenyl)-9-methoxy-2-oxo-2,3-dihydro-1H-1,4-benzodiazepin-3-yl)-2,3-bis(3,3,3-trifluoropropyl)succinamide (45); (2R,3S)—N-((3S)-5-(4-(hydroxymethyl)phenyl)-2-oxo-2,3-dihydro-1H-1,4-benzodiazepin-3-yl)-2,3-bis(3,3,3-trifluoropropyl)succinamide (46); (2R,3S)—N-((3S)-5-(2-methylphenyl)-2-oxo-2,3-dihydro-1H-1,4-benzodiazepin-3-yl)-2,3-bis(3,3,3-trifluoropropyl)succinamide (47); (2R,3S)—N-((3S)-5-(3-methylphenyl)-2-oxo-2,3-dihydro-1H-1,4-benzodiazepin-3-yl)-2,3-bis(3,3,3-trifluoropropyl)succinamide (48); (2R,3S)—N-((3S)-9-methoxy-2-oxo-5-(5-(trifluoromethyl)-2-pyridinyl)-2,3-dihydro-1H-1,4-benzodiazepin-3-yl)-2,3-bis(3,3,3-trifluoropropyl)succinamide (49); (2R,3S)—N-((3S)-5-(5-chloro-2-pyridinyl)-9-methoxy-2-oxo-2,3-dihydro-1H-1,4-benzodiazepin-3-yl)-2,3-bis(3,3,3-trifluoropropyl)succinamide (50); (2R,3S)—N-((3S)-5-(4-methoxyphenyl)-2-oxo-2,3-dihydro-1H-1,4-benzodiazepin-3-yl)-2,3-bis(3,3,3-trifluoropropyl)succinamide (51); (2R,3S)—N-((3S)-5-(4-methylphenyl)-2-oxo-2,3-dihydro-1H-1,4-benzodiazepin-3-yl)-2,3-bis(3,3,3-trifluoropropyl)succinamide (52); (2R,3S)—N-((3S)-5-(3-fluorophenyl)-9-(hydroxymethyl)-2-oxo-2,3-dihydro-1H-1,4-benzodiazepin-3-yl)-2,3-bis(3,3,3-trifluoropropyl)succinamide (53); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valinate (54); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-alaninate (55); S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteine (56); tert-butyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (57); methyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl) hexanoyl)amino)-L-cysteinate (58); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl (4-(phosphonooxy)phenyl) acetate (59); and ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valyl-L-valinate (60); and salts thereof.

In another embodiment, the present invention provides compositions comprising compounds represented by the structure of Formula (I):

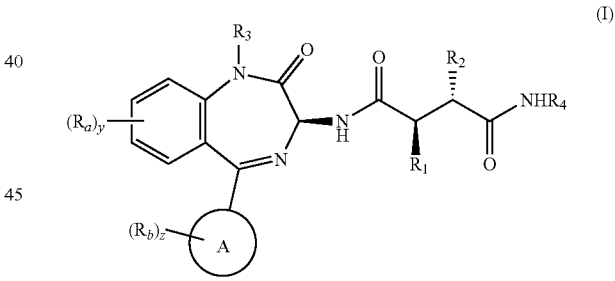

and/or at least one salt thereof, wherein:

$R_1$ is —CH$_2$CF$_3$ or —CH$_2$CH$_2$CF$_3$;

$R_2$ is —CH$_2$CF$_3$, —CH$_2$CH$_2$CF$_3$, or —CH$_2$CH$_2$CH$_2$CF$_3$;

$R_3$ is H, —CH$_3$ or Rx;

$R_4$ is H or $R_y$;

$R_x$ is: —CH$_2$OC(O)CH(CH$_3$)NH$_2$, —CH$_2$OC(O)CH(NH$_2$)CH(CH$_3$)$_2$, —CH$_2$OC(O)CH((C

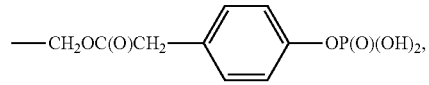

-continued

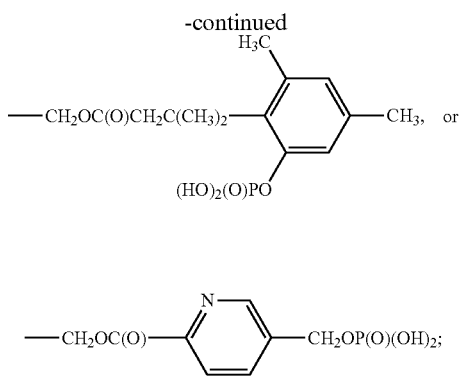

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;

Ring A is phenyl or pyridinyl;

each $R_a$ is independently F, Cl, —CN, —OCH$_3$, C$_{1-3}$ alkyl, —CH$_2$OH, —CF$_3$, cyclopropyl, —OCH$_3$, —O(cyclopropyl) and/or —NHCH$_2$CH$_2$OCH$_3$;

each $R_b$ is independently F, Cl, —CH$_3$, —CH$_2$OH, —CF$_3$, cyclopropyl, and/or —OCH$_3$;

y is zero, 1 or 2; and z is zero, 1, or 2 provided that if Ring A is phenyl, z is zero, and y is 1 or 2 then at least one $R_a$ is C$_{1-3}$ alkyl, —CH$_2$OH, —CF$_3$, cyclopropyl, or —O(cyclopropyl);

provided that if $R_3$ is $R_x$ then $R_4$ is H; and provided that if $R_4$ is $R_y$, then $R_3$ is H or —CH$_3$.

In another embodiment, a structure as described hereinabove comprises one or more of the following provisos: provided that if Ring A is phenyl, z is zero, and y is 1 or 2 then at least one $R_a$ is C$_{1-3}$ alkyl, —CH$_2$OH, —CF$_3$, cyclopropyl, or —O(cyclopropyl); provided that if $R_3$ is $R_x$ then $R_4$ is H; and provided that if $R_4$ is $R_y$, then $R_3$ is H or —CH$_3$.

In another embodiment, the present invention provides compositions comprising compounds represented by the following structure:

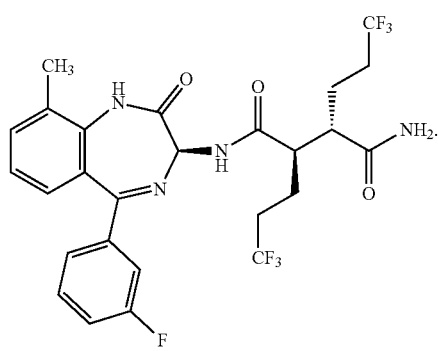

(22)

In another embodiment, the compounds as described herein comprise prodrugs of one or more of the compounds.

U.S. Pat. No. 9,273,014, which is incorporated herein in its entirety, discloses various compounds of Formula (I):

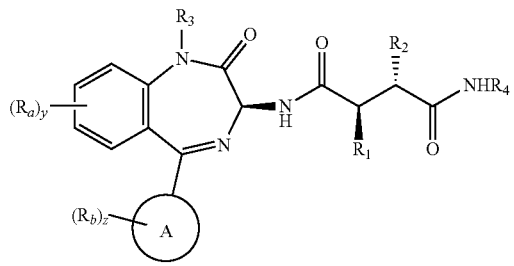

(I)

and/or at least one salt thereof, wherein:

$R_1$ is —CH$_2$CH$_2$CF$_3$;

$R_2$ is —CH$_2$CH$_2$CF$_3$ or —CH$_2$CH$_2$CH$_2$CF$_3$;

$R_3$ is H, —CH$_3$, or Rx;

$R_4$ is H or $R_y$;

$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH(C

H$_3$)$_2$)NHC(O)CH(NH$_2$)CH(CH$_3$)$_2$,

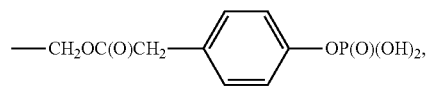

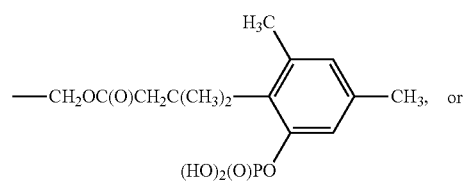

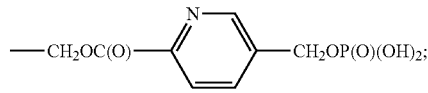

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;

Ring A is phenyl or pyridinyl;

each $R_a$ is independently Cl, C$_{1-3}$ alkyl, —CH$_2$OH, —CF$_3$, cyclopropyl, —OCH$_3$, and/or —O(cyclopropyl);

each $R_b$ is independently F, Cl, —CH$_3$, —CH$_2$OH, —CF$_3$, cyclopropyl, and/or —OCH$_3$;

y is zero, 1, or 2; and z is 1 or 2.

U.S. Pat. No. 9,273,014 also discloses the compound of Formula (22):

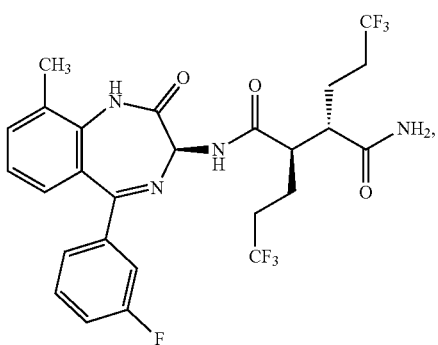

(22)

which, in one embodiment, has the chemical name (2R, 3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide. U.S. Pat. No. 9,273,014 also discloses a process for synthesizing the compounds as well as other compounds of Formula (I), which are to be considered as part of the present invention.

U.S. Pat. No. 8,629,136, which is incorporated by reference herein in its entirety, discloses compounds of Formula (III):

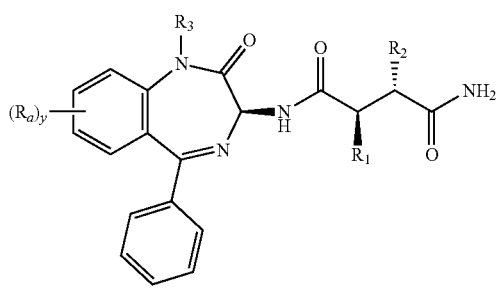

(III)

and/or at least one salt thereof, wherein:
$R_3$ is H or —$CH_3$; and
each $R_a$ is independently F, Cl, —CN, —$OCH_3$ and/or —$NHCH_2CH_2OCH_3$.

U.S. Pat. No. 8,629,136 also discloses the compound of Formula (1):

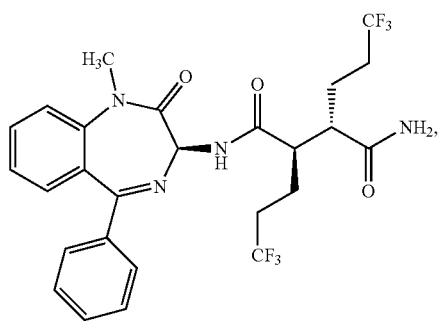

(1)

which, in one embodiment, has the chemical name (2R, 3S)—N-((3S)-1-methyl-2-oxo-5-phenyl-2,3-dihydro-1H-1,4-benzodiazepin-3-yl)-2,3-bis(3,3,3-trifluoropropyl)succinamide. In one embodiment, the compounds are Notch inhibitors. U.S. Pat. No. 8,629,136 discloses a process for synthesizing the compounds as well as other compounds of Formula (I), which are to be considered as part of the present invention.

In one embodiment, the present invention provides compositions comprising compounds as described herein formulated at a dose of 4 mg. In one embodiment, the present invention provides compositions comprising compounds as described herein formulated for intravenous administration.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

Combined Treatments

In one embodiment, compositions of the present invention or for use in the methods of the present invention comprise one or more cancer therapeutic agents in combination with one or more bisfluoroalkyl-1,4-benzodiazepinone compounds described hereinabove.

In treating cancer, a combination of chemotherapeutic agents and/or other treatments (e.g., radiation therapy) is often advantageous. An additional agent may have the same or different mechanism of action than the primary therapeutic agents. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof a composition as described herein and administering one or more anti-cancer agents.

In one embodiment, the phrase "anti-cancer agent" refers to a drug selected from any one or more of the following: alkylating agents (including nitrogen mustards, methanesulphonate, busulphan, alkyl sulfonates, nitrosoureas, ethylenimine derivatives, and triazenes, or a combination thereof); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/ab1, cyclin dependent kinase [CDK] inhibitors, panHer, Her-1 and Her-2 antibodies, VEGF inhibitors, including anti-VEGF antibodies, EGFR inhibitors, PARP (poly ADP-ribose polymerase) inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, platinum-based antineoplastic drugs (platins) such as cisplatin, carboplatin, oxaliplatin, nedaplatin, triplatin tetranitrate, phenanthriplatin, picoplatin and satraplatin, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

In one embodiment, a composition of the present invention comprises one or more compounds represented by the structure of Formula (I) as described herein and one or more targeted therapeutic. In one embodiment, said targeted therapeutic comprises an inhibitor of mammalian target of rapamycin (mTOR). In one embodiment, the mTOR inhibitor comprises Everolimus. In another embodiment, the mTOR inhibitor comprises sirolimus (rapamycin). In another embodiment, the mTOR inhibitor comprises temsirolimus.

In another embodiment, the mTOR inhibitor comprises a dual mammalian target of rapamycin/phosphoinositide 3-kinase inhibitor, which in one embodiment, comprises NVP-BEZ235 (dactolisib), GSK2126458, XL765, or a combination thereof.

In another embodiment, the mTOR inhibitor comprises a second generation mTOR inhibitor, which, in one embodiment, comprises AZD8055, INK128/MLN0128, OSI027, or a combination thereof.

In another embodiment, the mTOR inhibitor comprises a third generation mTOR inhibitor, which, in one embodiment, comprises RapaLinks.

In one embodiment, a composition of the present invention comprises one or more compounds represented by the structure of Formula (I) as described herein in combination with an mTOR inhibitor and a chemotherapeutic drug. In one embodiment, the mTOR inhibitor comprises everolimus. In one embodiment, the chemotherapeutic drug comprises cisplatin.

In one embodiment, a composition of the present invention comprises one or more compounds represented by the structure of Formula (I) as described herein in combination with a PARP (poly ADP-ribose polymerase) inhibitor.

In another embodiment, a composition of the present invention comprises one or more compounds represented by the structure of Formula (I) as described herein and a polyfunctional alkylating agent. In one embodiment, the polyfunctional alkylating agent comprises a Nitrosourea, Mustard, Nitrogen Mustard, Methanesulphonate, Busulphan, Ethylenimine, or a combination thereof.

In another embodiment, a composition of the present invention comprises one or more compounds represented by the structure of Formula (I) as described herein in combination with steroids.

In another embodiment, a composition of the present invention comprises one or more compounds represented by the structure of Formula (I) as described herein in combination with bisphosphonates.

In another embodiment, a composition of the present invention comprises one or more compounds represented by the structure of Formula (I) as described herein in combination with cancer growth blockers.

In another embodiment, a composition of the present invention comprises one or more compounds represented by the structure of Formula (I) as described herein in combination with proteasome inhibitors.

In another embodiment, a composition of the present invention comprises one or more compounds represented by the structure of Formula (I) as described herein in combination with one or more interferons.

In another embodiment, a composition of the present invention comprises one or more compounds represented by the structure of Formula (I) as described herein in combination with one or more interleukins.

In another embodiment, the present invention provides a composition comprising one or more compounds represented by the structure of Formula (I) as described herein and an alkylating drug. In one embodiment, the alkylating drug comprises Procarbazine (MATULANE®), Dacarbazine (DTIC), Altretamine (HEXALEN®), or a combination thereof.

In another embodiment, the present invention provides a composition comprising one or more compounds represented by the structure of Formula (I) as described herein and an alkylating-like drug. In one embodiment, the alkylating-like drug comprises Cisplatin (Platinol).

In another embodiment, the present invention provides a composition comprising one or more compounds represented by the structure of Formula (I) as described herein and an antimetabolite. In one embodiment, the antimetabolite comprises an antifolic acid compound (Methotrexate), an amino acid antagonists (Azaserine), or a combination thereof.

In another embodiment, the present invention provides a composition comprising one or more compounds represented by the structure of Formula (I) as described herein and a purine antagonist. In one embodiment, the purine antagonist comprises Mercaptopurine (6-MP), Thioguanine (6-TG), Fludarabine Phosphate, Cladribine (LEUSTATIN®), Pentostatin (NIPENT®), or a combination thereof.

In another embodiment, the present invention provides a composition comprising one or more compounds represented by the structure of Formula (I) as described herein and a pyrimidine antagonist. In one embodiment, the pyrimidine antagonist comprises Fluorouracil (5-FU), Cytarabine (ARA-C), Azacitidine, or a combination thereof.

In another embodiment, the present invention provides a composition comprising one or more compounds represented by the structure of Formula (I) as described herein and a plant alkaloid. In one embodiment, the plant alkaloid comprises Vinblastine (VELBAN®), Vincristine (ONCOVIN®), Etoposide (VP-16, VEPE-SID®), Teniposide (VUMON®), Topotecan (HYCAMTIN®), Irinotecan (CAMPTOSAR®), Paclitaxel (TAXOL®), Docetaxel (TAXOTERE®), or a combination thereof.

In another embodiment, the present invention provides a composition comprising one or more compounds represented by the structure of Formula (I) as described herein and FOLFIRI, wherein in one embodiment FOLFIRI comprises folinic acid (leucovorin), fluorouracil (5-FU) and irinotecan (CAMPTOSAR®). In another embodiment, the present invention provides a composition comprising one or more compounds represented by the structure of Formula (I) and an anti-CD20 agent as described herein in combination with folinic acid (leucovorin), fluorouracil (5-FU), irinotecan (CAMPTOSAR®), or a combination thereof.

In another embodiment, the present invention provides a composition comprising one or more compounds represented by the structure of Formula (I) as described herein and an antibiotic. In one embodiment, the antibiotic comprises Anthracyclines, Doxorubicin (ADRIAMYCIN, RUBEX, DOXIL®), Daunorubicin (DAUNOXOME®), Dactinomycin (COSMEGEN®), Idarubicin (IDAMYCIN®), Plicamycin (MITHRAMYCIN®), Mitomycin (MUTAMYCIN®), Bleomycin (BLENOXANE®), or a combination thereof.

In another embodiment, the present invention provides a composition comprising one or more compounds represented by the structure of Formula (I) as described herein in combination with a cancer vaccine. In another embodiment, the present invention provides a composition comprising one or more compounds represented by the structure of Formula (I) as described herein and an immunotherapeutic. In one embodiment, the immunotherapeutic comprises a monoclonal antibody. In one embodiment, the monoclonal antibody comprises an anti-PD-1 antibody, which in one embodiment comprises nivolumab.

In another embodiment, the monoclonal antibody comprises alemtuzumab (CAMPATH®), trastuzumab (HERCEPTIN®), Bevacizumab (AVASTIN®), Cetuximab (ERBITUX®), or a combination thereof. In another embodiment, the monocolonal antibody comprises a radiolabeled antibody, which, in one embodiment, comprises britumomab, tiuxetan (ZEVALIN®), or a combination thereof. In another embodiment, the monocolonal antibody comprises a chemolabeled antibody, which in one embodiment comprises Brentuximab vedotin (ADCETRIS®), Ado-trastuzumab emtansine (KADCYLA®, also called TDM-1), denileukin diftitox (ONTAK®), or a combination thereof. In another embodiment, the monocolonal antibody comprises a bispecific antibody, which in one embodiment, comprises blinatumomab (BLINCYTO®).

In another embodiment, the present invention provides a composition comprising one or more compounds represented by the structure of Formula (I) as described herein in combination with a hormonal therapy. In another embodiment, the present invention provides a composition comprising one or more compounds represented by the structure of Formula (I) as described herein and a hormonal agent. In one embodiment, the hormonal agent comprises Tamoxifen (NOLVADEX®), Flutamide (EULEXIN®), Gonadotropin-Releasing Hormone Agonists, (Leuprolide and Goserelin (ZOLADEX®)), Aromatase Inhibitors, Aminoglutethimide, Anastrozole (ARIMIDEX®), or a combination thereof.

In another embodiment, the present invention provides a composition comprising one or more compounds represented by the structure of Formula (I) as described herein and Amsacrine, Hydroxyurea (Hydrea), Asparaginase (ELSPAR®), Mitoxantrone (NOVANTRONE®), Mitotane, Retinoic Acid Derivatives, Bone Marrow Growth Factors, Amifostine, or a combination thereof. In one embodiment, the retinoic acid derivative comprises all-trans retinoic acid (ATRA).

In another embodiment, the monoclonal antibody comprises alemtuzumab (CAMPATH®), trastuzumab (HERCEPTIN®), Bevacizumab (AVASTIN®), Cetuximab (ERBITUX®), or a combination thereof. In another embodiment, the monocolonal antibody comprises a radiolabeled antibody, which, in one embodiment, comprises britumomab, tiuxetan (ZEVALIN®), or a combination thereof. In another embodiment, the monocolonal antibody comprises a chemolabeled antibody, which in one embodiment comprises Brentuximab vedotin (ADCETRIS®), Ado-trastuzumab emtansine (KADCYLA®, also called TDM-1), denileukin diftitox (ONTAK®), or a combination thereof. In another embodiment, the monocolonal antibody comprises a bispecific antibody, which in one embodiment, comprises blinatumomab (BLINCYTO®).

In another embodiment, the present invention provides a composition comprising one or more compounds represented by the structure of Formula (I) as described herein in combination with a hormonal therapy. In another embodiment, the present invention provides a composition comprising one or more compounds represented by the structure of Formula (I) as described herein and a hormonal agent. In one embodiment, the hormonal agent comprises Tamoxifen (NOLVADEX®), Flutamide (EULEXIN®), Gonadotropin-Releasing Hormone Agonists, (Leuprolide and Goserelin (ZOLADEX®)), Aromatase Inhibitors, Aminoglutethimide, Anastrozole (ARIMIDEX®), or a combination thereof.

In another embodiment, the present invention provides a composition comprising one or more compounds represented by the structure of Formula (I) as described herein and Amsacrine, Hydroxyurea (Hydrea), Asparaginase (ELSPAR®), Mitoxantrone (NOVANTRONE®), Mitotane, Retinoic Acid Derivatives, Bone Marrow Growth Factors, Amifostine, or a combination thereof. In one embodiment, the retinoic acid derivative comprises all-trans retinoic acid (ATRA).

In another embodiment, the present invention provides a composition comprising one or more compounds represented by the structure of Formula (I) as described herein in combination with an agent that inhibits one or more cancer stem cell pathways. In one embodiment, such agent comprises an inhibitor of Hedgehog, WNT, BMP, or a combination thereof.

In one embodiment, said anti-cancer agent comprises a BCMA-targeted chimeric antigen receptor T-cell immunotherapeutic, p53-HDM2 inhibitor, c-MET inhibitor, BCR-ABL inhibitor, Anti-interleukin-1 beta monoclonal antibody, EGFR mutation modulator, PI3K-alpha inhibitor, JAK1/2 inhibitor, Cortisol synthesis inhibitor, Thrombopoietin, P-selectin inhibitor receptor agonist, Anti-CD20 monoclonal antibody, Anti-PD-1 monoclonal antibody, Signal transduction inhibitor, CDK4/6 inhibitor, BRAF inhibitor+MEK inhibitor, CD19-targeted chimeric antigen receptor T-cell immunotherapeutic, Somatostatin analogue, or a combination thereof. In one embodiment, said anti-cancer agent comprises capmatinib, asciminib, canakinumab, alpelisib, ruxolitinib, osilodrostat, eltrombopag, crizanlizumab, ofatumumab, spartalizumab, midostaurin, ribociclib, dabrafenib+trametinib, tisagenlecleucel, everolimus, pasireotide, or a combination thereof.

In another embodiment, the present invention provides a composition comprising one or more compounds represented by the structure of Formula (I) as described herein in combination with a hematopoietic stem cell transplant approach.

In another embodiment, the present invention provides a composition comprising one or more compounds represented by the structure of Formula (I) as described herein in combination with isolated infusion approaches. In one embodiment, the isolated infusion approach comprises infusion of chemotherapy into a specific tissue in order to deliver a very high dose of chemotherapy to tumor sites without causing overwhelming systemic damage.

In another embodiment, the present invention provides a composition comprising one or more compounds represented by the structure of Formula (I) as described herein in combination with targeted delivery mechanisms. In one embodiment, the targeted delivery mechanism increases effective levels of chemotherapy for tumor cells while reducing effective levels for other cells for increased tumor specificity and/or reduced toxicity. In one embodiment, targeted delivery mechanisms comprise a traditional chemotherapeutic agent, or a radioisotope or an immune stimulating factor.

In another embodiment, the present invention provides a composition comprising one or more compounds represented by the structure of Formula (I) as described herein in combination with Nanoparticles. In one embodiment, nanoparticles are used as a vehicle for poorly-soluble agents such as paclitaxel. In one embodiment, nanoparticles made of magnetic material can also be used to concentrate agents at tumour sites using an externally applied magnetic field.

In another embodiment, the present invention provides a composition comprising one or more compounds represented by the structure of Formula (I) as described herein in combination with an agent for treating Adenoid Cystic Carcinoma (ACC). In one embodiment, said agent for treating ACC comprises Axitinib, Bortezomib (Velcade), Bortezomib+doxorubicin, Cetuximab, Cetuximab+Intensity modulated radiation therapy (IMRT), Cetuximab+RT+cisplatin, Cetuximab+cisplatin+5-FU, Chidamide (CS055/HBI-8000), Cetuximab & Carbon Ion, Cisplatin, cisplatin & 5-FU, Cisplatin & Doxorubicin & Bleomycin, Cisplatin & Doxorubicin & Cyclophosphamide, Dasatinib, Dovitinib, Epirubicin, Gefitinib, Gemcitabine, Gemcitabine & Cisplatin, Imatinib, Imatinib+cisplatin, Lapatinib, Mitoxanthrone, MK 2206, Nelfinavir, Paclitaxel, Paclitaxel & Carboplatin, Panitumumab & Radiotherapy, PF-00562271, PF-00299804 & Figitumumab PX-478, PX-866, Regorafenib, Sonepcizumab, Sorafenib, Sunitinib, Vinorelbine, Vinorelbine & Cisplatin, Vorinostat, XL147 & Erlotinib, XL647, or combinations thereof.

In another embodiment, the present invention provides a composition comprising one or more compounds represented by the structure of Formula (I) as described herein in combination with pembrolizumab, docetaxel, nivolumab and ipilimumab, PSMA-PET Imaging, chidamide, APG-115, HDM201, DS-3032b, LY3039478, or a combination thereof.

In another embodiment, the present invention provides a composition comprising one or more compounds represented by the structure of Formula (I) as described herein in combination with an agent for treating triple negative breast cancer. In one embodiment, said agent for treating triple negative breast cancer comprises PARP (poly ADP-ribose polymerase) inhibitors such as olaparib, VEGF (vascular endothelial growth factor) inhibitors such as bevacizumab, EGFR (epidermal growth factor receptor)-targeted therapies such as cetuximab, or a combination thereof.

In one embodiment, a method is provided for treating cancer comprising administering to a mammal in need thereof a composition as described herein and administering one or more anti-cancer agents.

In one embodiment, the phrase "anti-cancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, PARP (poly ADP-ribose polymerase) inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

In another embodiment, the present invention provides a composition comprising one or more compounds represented by the structure of Formula (I) as described herein in combination with any one or more of the following: REVLIMID®, AVASTIN®, HERCEPTIN®, RITUXAN®, OPDIVO®, GLEEVEC®, IMBRUVICA®, VELCADE®, ZYTIGA®, XTANDI®, ALIMTA®, GARDASIL®, IBRANCE®, PERJETA®, TASIGNA®, XGEVA®, AFINITOR®, JAKAFI®, TARCEVA®, KEYTRUDA®, SUTENT®, YERVOY®, NEXAVAR®, ZOLADEX®, ERBITUX®, DAZALEX®, XELODA®, GAZYVA®, VENCLEXTA® (aka ABT-199), and TECENTRIQ®.

In another embodiment, the present invention provides a composition comprising one or more compounds represented by the structure of Formula (I) as described herein in combination with any one or more of the following: abemaciclib, epacadostat, apalutamide, Carfilzomib, Crizotinib (PF-02341066), GDC-0449 (vismodegib), ONCOVEX$^{GM-CSF}$, PLX4032 (RG7204), Ponatinib, SGN-35 (brentuximab vedotin), Tivozanib (AV-951), T-DM1 (Trastuzumab-DM1), and XL184 (cabozantinib).

Accordingly, the compositions of the present invention may be administered in combination with other anti-cancer treatments useful in the treatment of cancer or other proliferative diseases. The invention herein further comprises use of the compositions of the present invention in preparing medicaments for the treatment of cancer, and/or it comprises the packaging of the compositions of the present invention together with instructions that the compositions be used in combination with other anti-cancer or cytotoxic agents and treatments for the treatment of cancer.

In one embodiment, a method is provided for treating cancer comprising administering to a mammal in need thereof a combination of a compound of Formula (I) and an additional anti-cancer agent, which is one embodiment, comprises an mTOR inhibitor; administering cisplatin; and optionally, one or more additional anti-cancer agents.

In one embodiment, a method is provided for treating cancer comprising administering to a mammal in need thereof a combination of a compound of Formula (I) and an additional anti-cancer agent, which is one embodiment, comprises an mTOR inhibitor; administering dasatinib; and optionally, one or more additional anti-cancer agents.

In one embodiment, a method is provided for treating cancer comprising administering to a mammal in need thereof a combination of a compound of Formula (I) and an additional anti-cancer agent, which is one embodiment, comprises an mTOR inhibitor; administering paclitaxel; and optionally, one or more additional anti-cancer agents.

In one embodiment, a method is provided for treating cancer comprising administering to a mammal in need thereof a combination of a compound of Formula (I) and an additional anti-cancer agent, which is one embodiment, comprises an mTOR inhibitor; administering Tamoxifen; and optionally, one or more additional anti-cancer agents.

In one embodiment, a method is provided for treating cancer comprising administering to a mammal in need thereof a combination of a compound of Formula (I) and an additional anti-cancer agent, which is one embodiment, comprises an mTOR inhibitor; administering a glucocorticoid; and optionally, one or more additional anti-cancer agents. An example of a suitable glucocorticoid is dexamethasone.

In one embodiment, a method is provided for treating cancer comprising administering to a mammal in need thereof a combination of a compound of Formula (I) and an additional anti-cancer agent, which is one embodiment, comprises an mTOR inhibitor; administering carboplatin; and optionally, one or more additional anti-cancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising a compound of Formula (I) or prodrug thereof; one or more additional agents selected from a kinase inhibitory agent (small molecule, polypeptide, and antibody), an immunosuppressant, an anti-cancer agent, an anti-viral agent, anti-inflammatory agent, antifungal agent, antibiotic, or an anti-vascular hyperproliferation compound; and any pharmaceutically or food grade acceptable carrier, adjuvant or vehicle.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Pharmaceutical Compositions
Formulations

Also embraced within this invention is a class of pharmaceutical compositions comprising the compound of Formula (I) and one or more non-toxic, pharmaceutically-acceptable carriers and/or diluents and/or adjuvants (collectively referred to herein as "carrier" materials) and, if desired, other active ingredients.

The compounds of Formula (I) may be administered by any suitable route, preferably in the form of a pharmaceutical composition adapted to such a route, and in a dose effective for the treatment intended. The compounds and compositions of the present invention may, for example, be administered in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.3 to 2000 mg, preferably from about 0.3 to 500 mg, and more preferably from about 5 to 150 mg. A suitable daily dose for a human or other mammal may vary widely depending on the condition of the patient and other factors, but, can be determined using routine methods. Moreover, if a particular dose is higher than desired or tolerated in a daily dosing regimen, dosing can be modified to achieve desired results by utilizing a modified appropriate dosing schedule, such as, for example, twice a week dosing or other suitable schedule. Such modifications and variations are within the scope and knowledge of the ordinarily skilled artisan.

Any pharmaceutical composition contemplated herein can, for example, be delivered orally via any acceptable and suitable oral preparations. Exemplary oral preparations, include, but are not limited to, for example, tablets, troches, lozenges, pills, aqueous and oily suspensions, dispersible powders, pellets or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. Tablet and other oral preparations also can include, without limitation, buccal, chewable, effervescent, modified release, orally disintegrating, sublingual, for oral solution, for oral suspension, triturates, or any other forms suitable for use in accordance with the compositions and methods described herein. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated or encapsulated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose, poly (meth) acrylate and cellulose acetate butyrate. Alternatively, if desired, a formulation can be prepared to include only drug substance.

Hard gelatin capsules can, for example, be prepared by mixing at least one compound of Formula (I) with at least one inert solid diluent, such as, for example, calcium carbonate; calcium phosphate; and kaolin. Alternatively, if desired, the capsule can be prepared to include only drug substance.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

In another embodiment, the compounds of Formula (I) can be formulated as a nanoparticle, lipid nanoparticle, microparticle or liposome.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

For example, the composition may be provided for intravenous administration comprising an amount of active ingredient in the range of from about 0.2 to 150 mg. In another embodiment, the active ingredient is present in the range of from about 0.3 to 10 mg. In another embodiment, the active ingredient is present in the range of from about 4 to 8.4 mg. In one embodiment, the active ingredient is administered at a dose of about 4 mg. In another embodiment, the active ingredient is administered at a dose of about 6 mg. In another embodiment, the active ingredient is administered at a dose of about 8.4 mg.

In another embodiment, the active ingredient is administered at a dose of about 0.3 mg. In another embodiment, the active ingredient is administered at a dose of about 0.6 mg. In another embodiment, the active ingredient is administered at a dose of about 1.2 mg. In another embodiment, the active ingredient is administered at a dose of about 2.4 mg.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in any suitable solvent, including, without limitation water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles, parenterally acceptable diluents, and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

A sterile injectable oil-in-water nano- or microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkyl-cyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, gender, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

In one embodiment, the compound is administered to the subject once a week. In another embodiment, the compound is administered to the subject once every two weeks.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The compound in accordance with Formula (I) can be administered by any means suitable for the condition to be treated, which can depend on the need for site-specific treatment or quantity of Formula (I) compound to be delivered. The compounds and compositions of the present invention may, for example, be administered orally, mucosally, or parentally including intravascularly, intraperitoneally, subcutaneously, intramuscularly, and intrasternally. In another embodiment, the compounds and compositions of the present invention are administered intravenously.

Methods of Use

In one embodiment, the present invention provides the use of the described compounds or compositions for treating, suppressing or inhibiting a proliferative disease in a subject. In another embodiment, the present invention provides a method of treating, suppressing or inhibiting a proliferative disease in a subject. comprising the step of administering to said subject a first composition comprising one or more gamma secretase inhibitors comprising a compound represented by the structure of Formula (I):

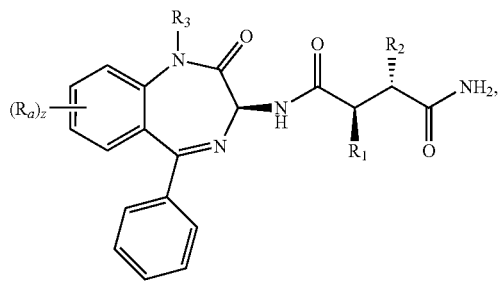

(I)

wherein:

R₁ is —CH₂CF₃ or —CH₂CH₂CF₃;

R₂ is —CH₂CF₃, —CH₂CH₂CF₃, or —CH₂CH₂CH₂CF₃;

R₃ is H or —CH₃;

each $R_a$ is independently F, Cl, —CN, —OCH₃, and/or —NHCH₂CH₂OCH₃; and z is zero, 1, or 2 and a second composition comprising an anti-cancer agent.

In one embodiment, the compound of Formula I comprises:

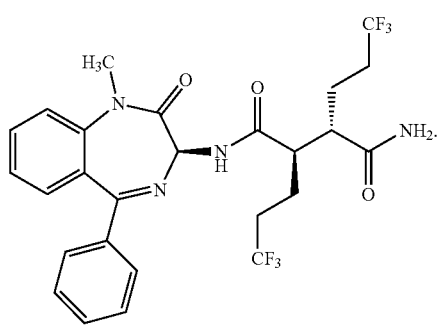

(1)

In another embodiment, the compound of Formula I comprises:

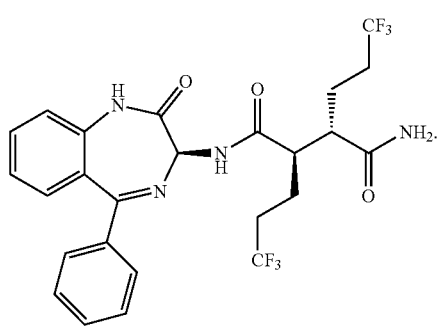

(2)

In another embodiment, the compound of Formula I comprises:

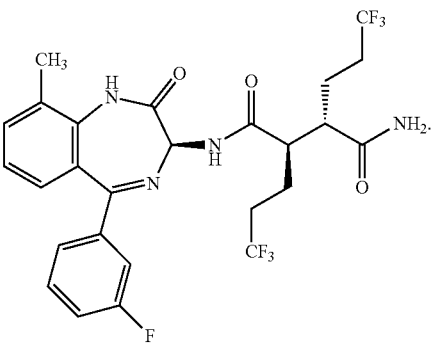

(22)

In one embodiment, a method is provided for treating a disease comprising a NOTCH activating mutation, comprising administering to a subject a compound of Formula (I) and an anti-cancer agent. In one embodiment, the NOTCH activating mutation is any NOTCH activating mutation. In one embodiment, the NOTCH activating mutation is a NOTCH1 activating mutation. In another embodiment, the NOTCH activating mutation is a NOTCH2 activating mutation. In another embodiment, the NOTCH activating mutation is a NOTCH3 activating mutation. In another embodiment, the NOTCH activating mutation is a NOTCH4 activating mutation.

In one embodiment, the disease comprises a lymphoid neoplasm. In another embodiment, the lymphoid neoplasm comprises a CD20 leukemia. In one embodiment, the lymphoid neoplasm comprises Chronic Lymphocytic Leukemia (CLL). In another embodiment, the lymphoid neoplasm comprises Small Lymphocytic Leukemia (SLL), mantle cell lymphoma (MCL), marginal zone lymphoma, diffuse large B-cell lymphoma (DLBCL), splenic diffuse red pulp small B-cell lymphoma, follicular lymphoma, or a combination thereof. In another embodiment, the lymphoid neoplasm comprises pediatric T-cell acute lymphoblastic leukemia/lymphoma (T-ALL), adult T-ALL, pediatric early T-cell precursor acute lymphoblastic leukemia (ETP-ALL), adult ETP-ALL, Adult T-cell leukemia/lymphoma, or a combination thereof. In another embodiment, the disease is associated with low CD20 expression levels in the subject. In one embodiment, the disease comprises Richter Syndrome. In another embodiment, the disease associated with low CD20 expression levels comprises Plasmablastic lymphoma, Primary effusion lymphoma, Large B-cell lymphoma arising from HHV8-associated multicentric Castleman's disease, ALK+large B cell lymphoma, or a combination thereof.

In one embodiment, the present invention provides the use of a therapeutically acceptable amount of one or more compounds or compositions as described herein for treating, suppressing or inhibiting a proliferative disease in a subject. In another embodiment, the present invention provides the use of a therapeutically effective amount of one or more compounds or compositions as described herein for treating, suppressing or inhibiting a proliferative disease in a subject. In another embodiment, the present invention provides the use of a synergistically effective amount of one or more compounds or compositions as described herein for treating, suppressing or inhibiting a proliferative disease in a subject. In another embodiment, the present invention provides the use of a synergistically therapeutically effective amount of one or more compounds or compositions as described herein for treating, suppressing or inhibiting a proliferative disease in a subject.

In one embodiment, the proliferative disease comprises a Desmoid tumor.

In one embodiment, the proliferative disease comprises a pre-cancerous condition or a benign proliferative disorder.

In one embodiment, the term "pre-cancerous" or, alternatively, "pre-malignant" as used herein interchangeably refers to diseases, syndromes or other conditions associated with an increased risk of cancer. Pre-cancer conditions in the context of the present invention include, but are not limited to: breast calcifications, vaginal intra-epithelial neoplasia, Barrett's esophagus, atrophic gastritis, dyskeratosis congenital, sideropenic dysphagia, lichen planus, oral submucous fibrosis, actinic keratosis, solar elastosis, cervical dysplasia, leukoplakia and erythroplakia.

In one embodiment, the term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting examples of benign hyperproliferative disorder are psoriasis and benign prostatic hyperplasia (BPH).

In another embodiment, the proliferative disease comprises a cancer.

In one embodiment, the cancer comprises a solid tumor. In another embodiment, the cancer comprises a hematological malignancy.

In one embodiment, a subject as described herein has cancer. In one embodiment, the term "cancer" in the context of the present invention includes all types of neoplasm whether in the form of solid or non-solid tumors and includes both malignant and premalignant conditions as well as their metastasis. In one embodiment, the cancer comprises a hematological malignancy.

In one embodiment, the cancer is a carcinoma, sarcoma, myeloma, leukemia, or lymphoma. In another embodiment, the cancer is a mixed type.

In one embodiment, Mixed Type cancers contain several types of cells. The type components may be within one category or from different categories. Some examples are: adenosquamous carcinoma; mixed mesodermal tumor; carcinosarcoma; teratocarcinoma.

In another embodiment, the cancer is dependent upon Notch activation. In another embodiment, the cancer comprises a Notch-activating mutation. In another embodiment, the cancer is not dependent upon Notch activation.

In another embodiment, the carcinoma comprises Adenoid Cystic Carcinoma (ACC).

In another embodiment, the carcinoma comprises Gastro-esophageal junction carcinoma.

In one embodiment, the carcinoma is an adenocarcinoma. In another embodiment, the carcinoma is a squamous cell carcinoma.

In one embodiment, the sarcoma comprises osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); and Mesenchymous or mixed mesodermal tumor (mixed connective tissue types).

In one embodiment, the cancer comprises myeloma, which, in one embodiment, is cancer that originates in the plasma cells of bone marrow. The plasma cells produce some of the proteins found in blood. In one embodiment, the cancer comprises multiple myeloma.

In another embodiment, the cancer comprises leukemia ("non-solid tumor" or "blood cancer"), which in one embodiment, is a cancer of the bone marrow (the site of blood cell production). In one embodiment, leukemia comprises myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); and Polycythemia vera or erythremia (malignancy of various blood cell products, but with red cells predominating).

In another embodiment, the cancer comprises T-cell acute lymphoblastic leukemia (T-ALL). In another embodiment, the cancer comprises T-lymphoblastic leukemia/lymphoma (TLL). In another embodiment, the cancer comprises Chronic Lymphocytic Leukemia (CLL).

In another embodiment, the cancer comprises a lymphoma. In one embodiment, the lymphoma comprises an extranodal lymphoma. In one embodiment, the lymphoma comprises a Hodgkin lymphoma. In another embodiment, the lymphoma comprises a Non-Hodgkin lymphoma.

In one embodiment, the breast cancer is triple negative breast cancer. In one embodiment, triple-negative breast cancer cells do not contain receptors for estrogen, progesterone or HER2. In one embodiment, breast cancer that is ER, PR and HER2 negative cannot be treated with hormone therapies or medications that work by blocking HER2, such as trastuzumab.

In another embodiment, the cancer is dependent upon Notch activation. In another embodiment, the cancer comprises a Notch-activating mutation. In another embodiment, the cancer is not dependent upon Notch activation.

In one embodiment, a cancer as described herein comprises a Notch activating genetic alteration. In another embodiment, a cancer as described herein comprises a Notch activating mutation. In another embodiment, a cancer as described herein comprises a Notch activating genetic mutation. In another embodiment, a cancer as described herein comprises a Notch mutation. In another embodiment, a cancer as described herein comprises a Notch altering mutation.

In one embodiment, Notch activating genetic alterations comprise a mutation in one or more Notch related genes. In one embodiment, the mutation in one or more Notch-related genes induces a gain of function (GOF) in Notch activity.

In another embodiment, the mutation in one or more Notch-related genes comprises a missense mutation. In another embodiment, the mutation in one or more Notch-related genes comprises a nonsense mutation. In another embodiment, the mutation in one or more Notch-related genes comprises an insertion mutation. In another embodiment, the mutation in one or more Notch-related genes comprises a deletion mutation. In another embodiment, the mutation in one or more Notch-related genes comprises a duplication mutation. In another embodiment, the mutation in one or more Notch-related genes comprises a frameshift mutation. In another embodiment, the mutation in one or more Notch-related genes comprises a repeat expansion. In another embodiment, the mutation in one or more Notch-related genes comprises a fusion.

In another embodiment, the cancer comprises astrocytoma, bladder cancer, breast cancer, cholangiocarcinoma (CCA), colon cancer, colorectal cancer, colorectal carcinoma, epithelial carcinoma, epithelial ovarian cancers, fibrosarcoma, gall bladder cancer, gastric cancer, glioblastoma, glioma, head and neck cancer, hepatocellular carcinoma, kidney cancer, liver cancer, lung cancer including non-small cell lung cancer (NSCLC), malignant fibrous histiocytoma (MFH), malignant pleural mesothelioma (MPM), medulloblastoma, melanoma, mesothelioma, neuroblastoma, osteosarcoma, ovarian adenocarcinoma, ovarian cancer, pancreatic adenocarcinoma, pancreatic cancer, prostate cancer, renal cell carcinoma (RCC), rhabdomyosarcoma, seminal vesicle cancer, and thyroid cancer. In one embodiment, the breast cancer is triple negative breast cancer.

As used herein, the term "cancer" includes the above categories of carcinoma, sarcoma, myeloma, leukemia, lymphoma and mixed type tumors. In particular, the term cancer includes: lymphoproliferative disorders, breast cancer, ovarian cancer, prostate cancer, cervical cancer, endometrial cancer, lung cancer, bone cancer, liver cancer, stomach cancer, bladder cancer, colon cancer, colorectal cancer, pancreatic cancer, cancer of the thyroid, head and neck cancer, cancer of the central nervous system, brain cancer, cancer of the peripheral nervous system, skin cancer, kidney cancer, as well as metastases of all the above. More particularly, as used herein the term may refer to: hepatocellular carcinoma, hematoma, hepatoblastoma, rhabdomyosarcoma, esophageal carcinoma, thyroid carcinoma, ganglioblastoma, glioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, Waldenstrom's Macroglobulinemia.

In another embodiment, the administration of the combined compositions as described herein reduces growth of the cells of a solid tumor or hematological malignancy by 40%, 50%, 60%, 70%, 80%, 90% or 95% compared to growth of the cells of the solid tumor or hematological malignancy that have not been treated with the combined compositions, i.e. have been treated with either one of the compositions, have been treated via a different cancer treatment, or have not been treated.

In another embodiment, the present invention provides methods of increasing or lengthening survival of a subject having a neoplasia. As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

In one embodiment, a subject as described herein is being treated with or has been previously treated with radiation therapy, chemotherapy, transplantation, immunotherapy, hormone therapy, or photodynamic therapy.

In one embodiment, a method is provided for treating cancer comprising administering to a mammal in need thereof a combination of a compound of Formula (I) and one or more anti-cancer agents. In one embodiment, the anti-cancer agent comprises Chlorambucil, Fludarain, Pentostatin, Ciclophosphamide, HDMP, Bendamustine, or a combination thereof.

In another embodiment, the anti-cancer agent comprises cisplatin, dasatinib, paclitaxel, tamoxifen, or a combination thereof.

In one embodiment, the "anti-cancer agent" or "additional anti-cancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/ab1, cyclin dependent kinase [CDK] inhibitors, panHer, Her-1 and Her-2 antibodies, VEGF inhibitors, including anti-VEGF antibodies, EGFR inhibitors, PARP (poly ADP-ribose polymerase) inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

In one embodiment, a method is provided for treating cancer comprising administering to a mammal in need thereof a combination of a compound of Formula (I) and an anti-cancer agent, which in one embodiment, comprises a glucocorticoid; and optionally, one or more additional anti-cancer agents. An example of a suitable glucocorticoid is dexamethasone.

In one embodiment, a method is provided for treating cancer comprising administering to a mammal in need thereof a combination of a compound of Formula (I) an anti-cancer agent, which in one embodiment, comprises carboplatin; and optionally, one or more additional anti-cancer agents.

Specific regimens of the methods of treating, suppressing or inhibiting a disease in a subject and the uses of the described compounds or compositions for increasing the efficacy of therapies as described herein can be varied as appropriate by one of skill in the art without departing from the scope of the invention. One of ordinary skill in the art would readily be able to determine a suitable treatment plan in accordance with the invention, based on the individual's needs. Factors to consider in determining such plans include, without limitation, the subject's mutational status, age, and comorbidities, as well as various other factors readily recognized by the ordinarily skilled artisan.

Definitions

Unless specifically stated otherwise herein, references made in the singular may also include the plural. For example, "a" and "an" may refer to either one, or one or more.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

As used herein, the term "administering" refers to bringing in contact with a compound of the present invention. In one embodiment, the compositions are applied locally. In another embodiment, the compositions are applied systemically. Administration can be accomplished to cells or tissue cultures, or to living organisms, for example humans.

As used herein, the terms "administering," "administer," or "administration" refer to delivering one or more compounds or compositions to a subject parenterally, enterally, or topically. Illustrative examples of parenteral administration include, but are not limited to, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. Illustrative examples of enteral administration include, but are not limited to oral, inhalation, intranasal, sublingual, and rectal administration. Illustrative examples of topical administration include, but are not limited to, transdermal and vaginal administration. In particular embodiments, an agent or composition is administered parenterally, optionally by intravenous administration or oral administration to a subject.

In one embodiment, a composition of the present invention comprises a pharmaceutically acceptable composition. In one embodiment, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, a composition of the present invention is administered in a therapeutically effective amount. In one embodiment, a "therapeutically effective amount" is intended to include an amount of a compound of the present invention alone or an amount of the combination of compounds claimed or an amount of a compound of the present invention in combination with other active ingredients effective to act as an inhibitor to a NOTCH receptor, effective to inhibit gamma secretase, or effective to treat or prevent proliferative diseases such as cancer. In one embodiment, a "therapeutically effective amount" of a composition of the invention is that amount of composition which is sufficient to provide a beneficial effect to the subject to which the composition is administered.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the term "decreasing the size of the tumor" as used herein is assessed using the "Response Evaluation Criteria In Solid Tumors" (RECIST). In one embodiment, RECIST measures reduction in tumor size by measuring the longest dimension of a target lesion. In one embodiment, the target lesion is selected on the basis of its size (lesion with the longest diameter) and its suitability for accurate repeated measurements (either by imaging techniques or clinically). In one embodiment, all other lesions (or sites of disease) are identified as non-target lesions and are also recorded at baseline. Measurements of these lesions are not required, but the presence or absence of each is noted throughout follow-up.

In one embodiment, the term "decreasing the volume of the tumor" as used herein is assessed using the radiological tumor response evaluation criteria. Whereby, the tumor is measured in two dimensions its maximum diameter (width) in the translation plane and its largest perpendicular diameter on same image (thickness), according to the World Health Organization (WHO).

According to any of the methods of the present invention and in one embodiment, a subject as described herein is human. In another embodiment, the subject is mammalian. In another embodiment, the subject is a primate, which in one embodiment, is a non-human primate. In another embodiment, the subject is murine, which in one embodiment is a mouse, and, in another embodiment is a rat. In another embodiment, the subject is canine, feline, bovine, equine, caprine, ovine, porcine, simian, ursine, vulpine, or lupine. In one embodiment, the subject is a chicken or fish.

In one embodiment, the compositions as described herein comprise the components of the composition (i.e., one or more anti-cancer agents and one or more gamma secretase inhibitors comprising a compound of Formula (I)) as described herein. In another embodiment, the compositions as described herein consist of the components of the composition (i.e., one or more anti-cancer agents and one or more gamma secretase inhibitors comprising a compound of Formula (I)) as described herein. In another embodiment, the compositions as described herein consist essentially of the components of the composition (i.e., one or more anti-cancer agents and one or more gamma secretase inhibitors comprising a compound of Formula (I)) as described herein.

It is to be understood that the compositions and methods of the present invention comprising the elements or steps as described herein may, in another embodiment, consist of those elements or steps, or in another embodiment, consist essentially of those elements or steps. In some embodiments, the term "comprise" refers to the inclusion of the indicated active agents, such as the anti-cancer agents and the gamma secretase inhibitor, as well as inclusion of other active agents, and pharmaceutically or physiologically acceptable carriers, excipients, emollients, stabilizers, etc., as are known in the pharmaceutical industry. In some embodiments, the term "consisting essentially of" refers to a composition, whose only active ingredients are the indicated active ingredients. However, other compounds may be included which are for stabilizing, preserving, etc. the formulation, but are not involved directly in the therapeutic effect of the indicated active ingredients. In some embodiments, the term "consisting essentially of" may refer to components which facilitate the release of the active ingredient. In some embodiments, the term "consisting" refers to a composition, which contains the active ingredients and a pharmaceutically acceptable carrier or excipient.

Timing and Site of Administration

In one embodiment, the administration of the anti-cancer agents occurs prior to, concurrent with, or following the administration of the compound of Formula (I).

In one embodiment, the administration of the anti-cancer agents occurs at the same site as the administration of the compound of Formula (I).

In one embodiment, the compound of Formula (I) is administered daily. In another embodiment, the compound of Formula (I) is administered 2 or 3 times per day. In another embodiment, the compound of Formula (I) is administered twice weekly. In another embodiment, the compound of Formula (I) is administered three, four, five, or six times per week. In another embodiment, the compound of Formula (I) is administered weekly. In another embodiment, the compound of Formula (I) is administered biweekly. In another embodiment, the compound of Formula (I) is administered once every three weeks. In another embodiment, the anti-cancer agent is administered once every three weeks. In one embodiment, the anti-cancer agent is administered until inhibition of disease progression is detected.

In one embodiment, the compound of Formula (I) is administered several days before and after the administration of the anti-cancer agent. In one embodiment, the compound of Formula (I) is administered 1, 2, 3, 4, or 5 days prior to the administration of the anti-cancer agent. In one embodiment, the compound of Formula (I) is administered 1, 2, 3, 4, or 5 days subsequent to the administration of the anti-cancer agent. In another embodiment, the compound of Formula (I) is administered one day before and up to 9 days following anti-cancer agent administration. In another embodiment, the compound of Formula (I) is administered one day before and on days 1, 8, and 9 following anti-cancer agent administration. In another embodiment, the compound of Formula (I) is administered one day before and 9 days following anti-cancer agent administration. In another embodiment, the compound of Formula (I) is administered one day before and daily for 9 days following anti-cancer agent administration. In another embodiment, the compound of Formula (I) is administered one day before and on day 9 following anti-cancer agent administration.

In some embodiments, one or more compositions of the present invention are administered at least once during a treatment cycle. In some embodiments, the compositions of the present invention are administered to the subject on the same days. In some embodiments, the compositions of the present invention are administered to the subject on the different days. In some embodiments, one or more compositions of the present invention are administered to the subject on the same days and on different days according to treatment schedules.

In particular embodiments, one or more compositions of the present invention are administered to the subject over one or more treatment cycles. A treatment cycle can be at least two, at least three, at least four, at least five, at least six, at least seven, at least 14, at least 21, at least 28, at least 48, or at least 96 days or more. In one embodiment, a treatment cycle is 28 days. In certain embodiments, the compositions are administered over the same treatment cycle or concurrently over different treatment cycles assigned for each composition. In various embodiments, the treatment cycle is determined by a health care professional based on conditions and needs of the subject.

In some embodiments, a composition is administered on at least one day, at least two days, at least three days, at least four days, at least five days, at least six days, at least seven days, at least eight days, at least nine days, at least ten days, at least eleven days, at least twelve days, at least 13 days, at least 14 days, at least 21 days, or all 28 days of a 28 day treatment cycle. In particular embodiments, a composition is administered to a subject once a day. In other particular embodiments, a composition is administered twice a day. In certain embodiments a composition is administered more than twice a day.

In one embodiment, one or more of the compositions as described herein are administered once per day. In another embodiment, one or more of the compositions as described herein are administered twice per day. In another embodiment, one or more of the compositions as described herein are administered three times per day. In another embodiment, one or more of the compositions as described herein are administered four times per day. In another embodiment, one or more of the compositions as described herein are administered once every two days, once every three days, twice a week, once a week, once every 2 weeks, once every 3 weeks.

In one embodiment, one or more of the compositions as described herein are administered for 7 days to 28 days. In another embodiment, one or more of the compositions as described herein are administered for 7 days to 8 weeks. In another embodiment, one or more of the compositions as described herein are administered for 7 days to 50 days. In another embodiment, one or more of the compositions as described herein are administered for 7 days to six months. In another embodiment, one or more of the compositions as described herein are administered for 7 days to one and half years. In another embodiment, one or more of the compositions as described herein are administered for 14 days to 12 months. In another embodiment, one or more of the compositions as described herein are administered for 14 days to 3 years. In another embodiment, one or more of the compositions as described herein are administered for several years. In another embodiment, one or more of the compositions as described herein are administered for one month to six months.

In one embodiment, one or more of the compositions as described herein are administered for 7 days. In another embodiment, one or more of the compositions as described herein are administered for 14 days. In another embodiment, one or more of the compositions as described herein are administered for 21 days. In another embodiment, one or more of the compositions as described herein are administered for 28 days. In another embodiment, one or more of the compositions as described herein are administered for 50 days. In another embodiment, one or more of the compositions as described herein are administered for 56 days. In another embodiment, one or more of the compositions as described herein are administered for 84 days. In another embodiment, one or more of the compositions as described herein are administered for 90 days. In another embodiment, one or more of the compositions as described herein are administered for 120 days.

The number of times a composition is administered to a subject in need thereof depends on the discretion of a medical professional, the disorder, the severity of the disorder, and the subject's response to the formulation. In some embodiments, a composition disclosed herein is administered once to a subject in need thereof with a mild acute condition. In some embodiments, a composition disclosed herein is administered more than once to a subject in need thereof with a moderate or severe acute condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition.

In the case wherein the subject's status does improve, upon the doctor's discretion the composition may administered continuously; or, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Kits

The present invention further comprises combinations of the compositions of the present invention and, optionally, one or more additional agents in kit form, e.g., where they are packaged together or placed in separate packages to be sold together as a kit, or where they are packaged to be formulated together.

In certain embodiments, the kit comprises a therapeutic or prophylactic composition containing an effective amount of an inhibitor of mammalian target of rapamycin (mTOR) in unit dosage form and an effective amount of the compound of Formula (I), as described herein. In particular embodiments, the cells further express at least one co-stimulatory ligand. In certain embodiments, the kit comprises a sterile container which contains therapeutic or prophylactic agents; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the composition(s) are provided together with instructions for administering the composition(s) to a subject having or at risk of developing a neoplasia (e.g., multiple myeloma). The instructions will generally include information about the use of the composition for the treatment or prevention of a neoplasia (e.g., multiple myeloma). In other embodiments, the instructions include at least one of the following: description of the therapeutic agent; dosage schedule and administration for treatment or prevention of a neoplasia (e.g., multiple myeloma) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

All patents, patent applications, and scientific publications cited herein are hereby incorporated by reference in their entirety.

The following example is presented in order to more fully illustrate the preferred embodiments of the invention. It should in no way be construed, however, as limiting the broad scope of the invention.

EXAMPLES

Methods

The ACC PDX models, ACC×9 and ACC×11 (Notch1 mutant, 3' tandem duplication) were evaluated. ACC×11 mice were randomly divided into control group (n=10) and 8 treatment groups (n=5-6). Control group was administered vehicle once every day for four consecutive days (qd×4). Compound (1) was dosed at 3.0 mg/kg orally, qd×4, ATRA dosed at 3 mg/kg, orally, once every day for five consecutive days (qd×5)); ABT-199 dosed at 100 mg/kg, orally, once a day (qd)); and Sorafenib dosed at 30 mg/kg, orally, qd, as single agents or each in combination with Compound (1). Dosing was initiated on Day 0. Tumor volume and animal weight were collected twice a week. PO=orally; qd=once a day; qwk=once a week; bid=twice a week; qd×4=4 days on/3 days off; qd×5=5 days on/2 days off.

Example 1

Treatment with Compound (1) Decreases Tumor Volume in Animal Models of ACC

Treatment of ACC animals with Compound (1) prevents growth of tumors compared to vehicle-treated animals (FIG. 1A).

Example 2

Figure 1B:
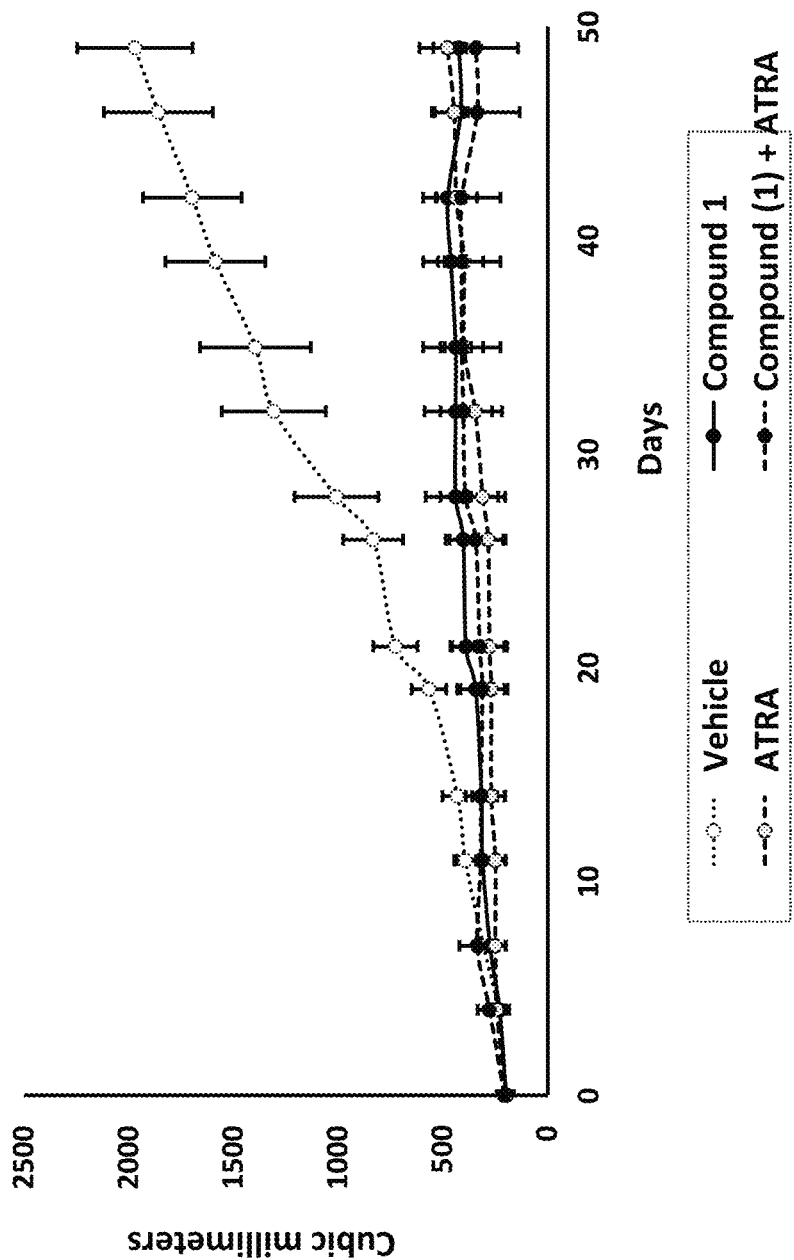
FIG. 1B. Tumor volume (Mean+/−SEM) over time in ACC animal models administered Compound (1) alone, ATRA alone, or a combination of Compound (1)+ATRA.

Treatment with a Combination of Compound (1), a Retinoic Acid Derivative, or a Combination in Animal Models of ACC Treatment of ACC animals with Compound (1), a retinoic acid derivative (ATRA), or with a combination of Compound (1)+ATRA prevents growth of tumors compared to vehicle-treated animals (FIG. 1B).

Example 3

Figure 1C:
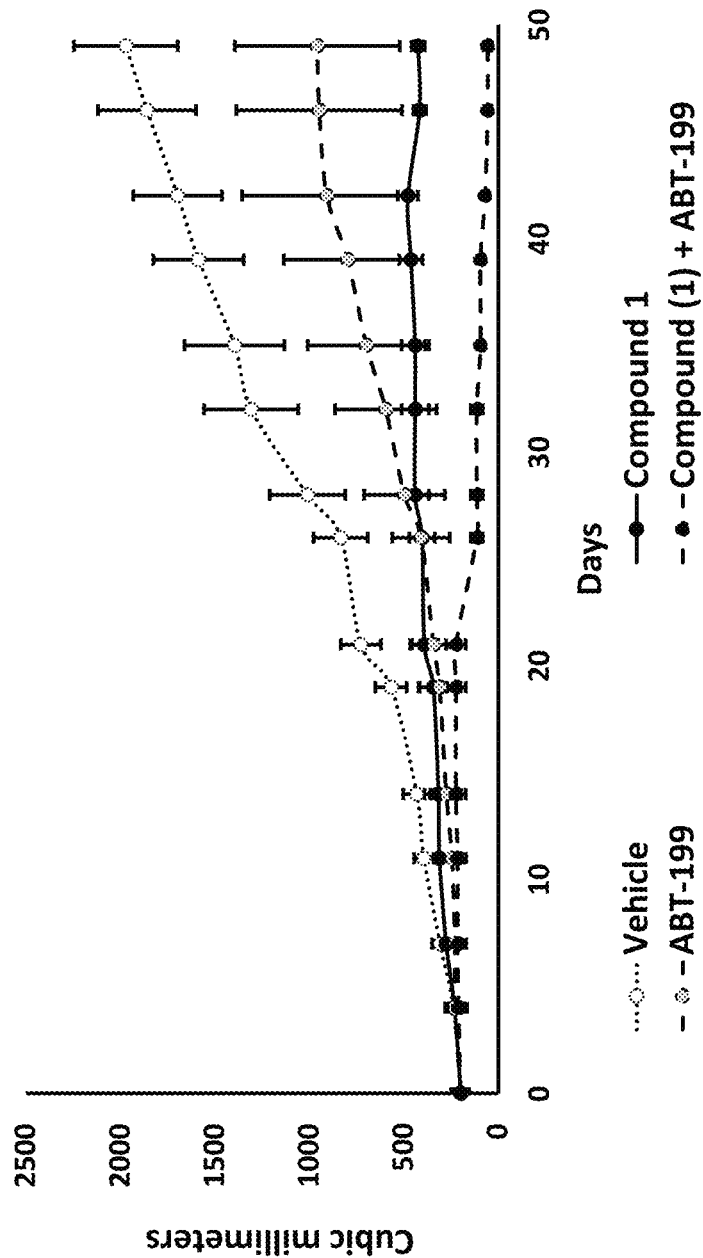
FIG. 1C. Tumor volume (Mean+/−SEM) over time in ACC animal models administered Compound (1) alone, ABT-199 alone, or a combination of Compound (1)+ABT-199.

Treatment with a Combination of Compound (1) and ABT-199 is More Effective than Either Treatment Alone in Animal Models of ACC Treatment of ACC animals with Compound (1), ABT-199, or with a combination of Compound (1)+ABT-199 prevents growth of tumors compared to vehicle-treated animals (FIG. 1C). The combination treatment is not only more effective than either treatment alone, but decreases tumor volume compared to tumor volume at the start of the experiment (FIG. 1C).

Example 4

Treatment with a Combination of Compound (1) and Sorafenib is More Effective than Either Treatment Alone in Animal Models of ACC Treatment of ACC animals with Compound (1), Sorafenib, or with a combination of Compound (1)+Sorafenib prevents growth of tumors compared to vehicle-treated animals (FIG. 1D). The combination treatment is not only more effective than either treatment alone, but decreases tumor volume compared to tumor volume at the start of the experiment (FIG. 1D).

Figure 2:
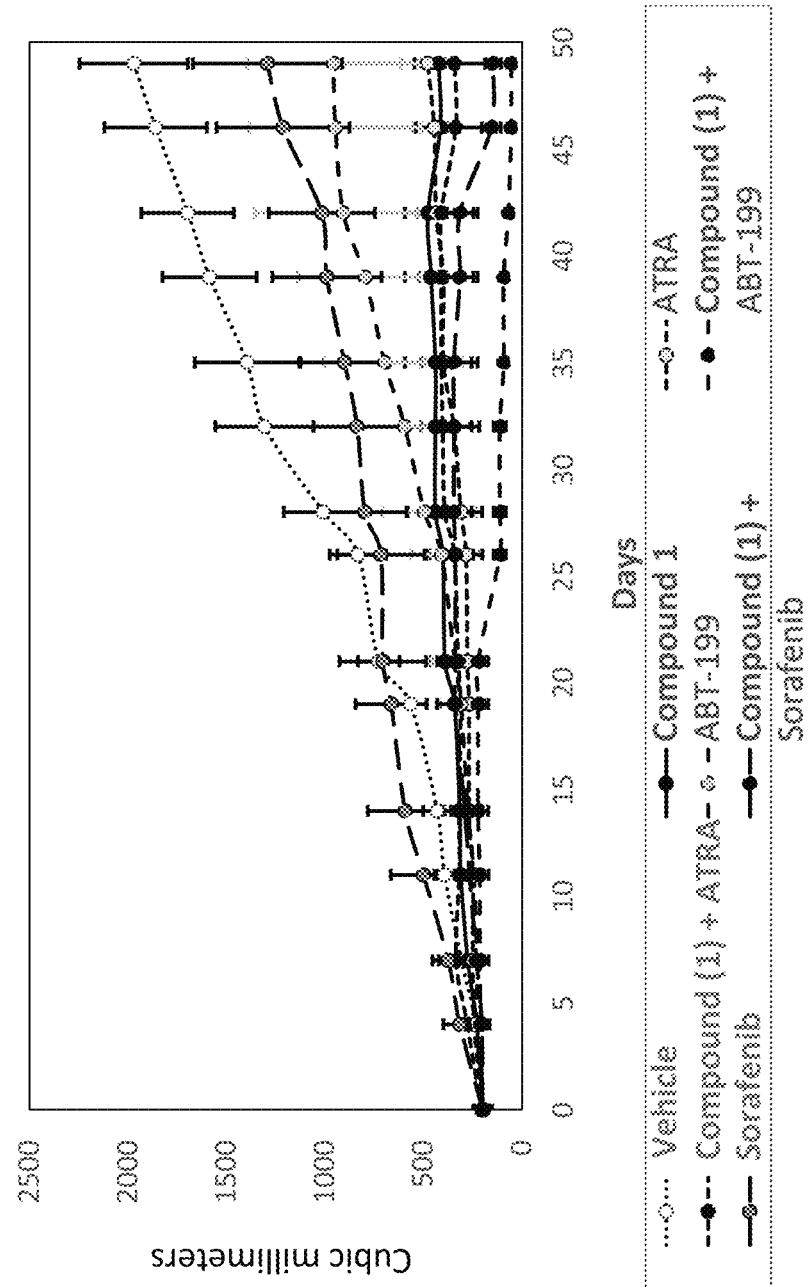
FIG. 2. Tumor volume (Mean+/−SEM) over time in ACC animal models in all treatment groups. Treatment groups: Vehicle; Compound (1) alone; ATRA alone; ATRA+Compound (1); ABT-199 alone; ABT-199+Compound (1); Sorafenib alone; or a combination of Compound (1)+Sorafenib.
Figure 3:
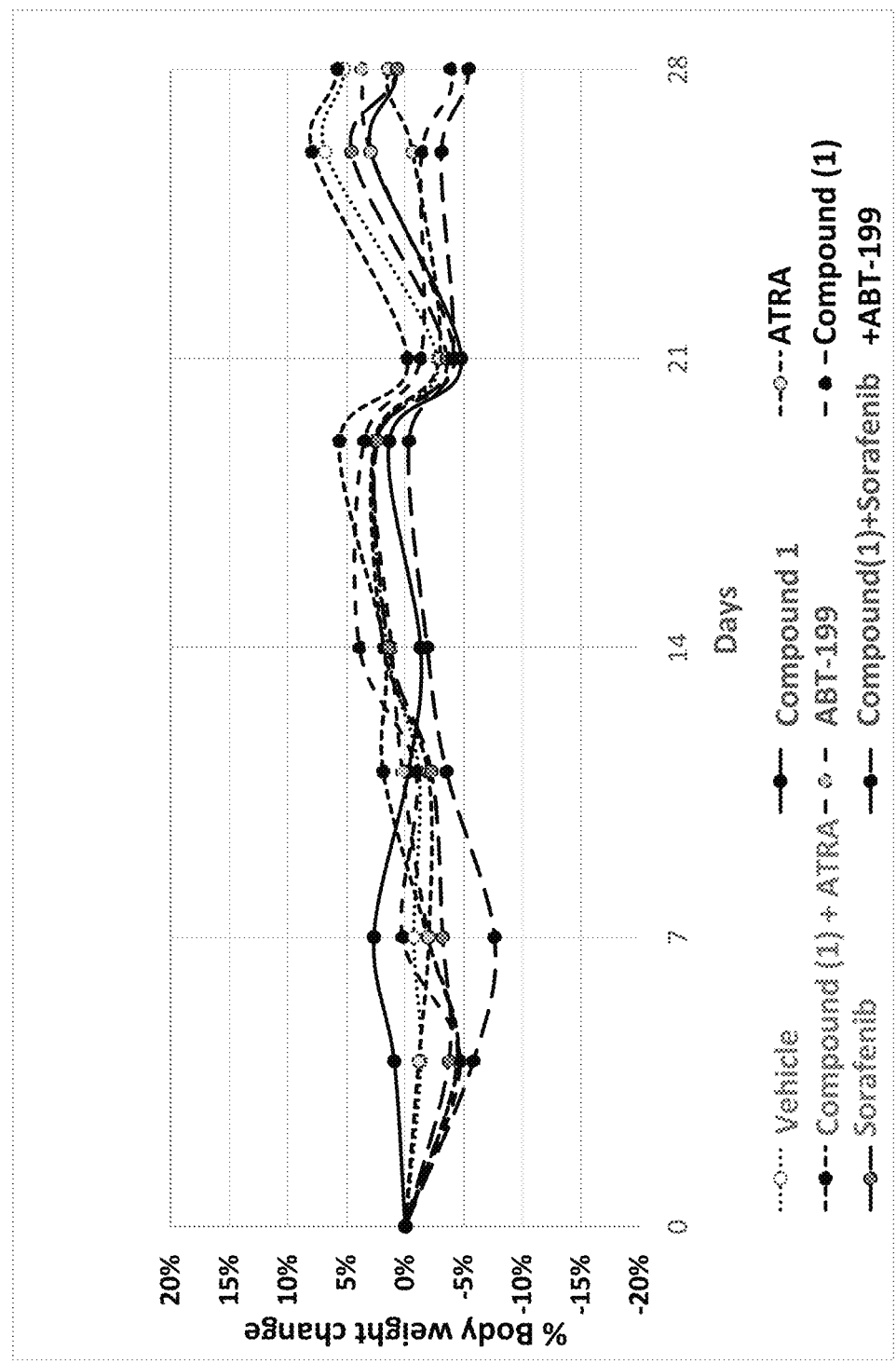
FIG. 3. Percent change in body weight for all treatment groups over time. Treatment groups: Vehicle; Compound (1) alone; ATRA alone; ATRA+Compound (1); ABT-199 alone; ABT-199+Compound (1); Sorafenib alone; or a combination of Compound (1)+Sorafenib.

Taken together, the combination of Compound (1) with other anti-cancer drugs reverses tumor growth in an experimental model of ACC (FIG. 2). In addition, there was no significant change in weight due to drug administration in any of the experimental groups (FIG. 3).

What is claimed is:

1. A composition comprising a compound represented by the structure of Compound (1):

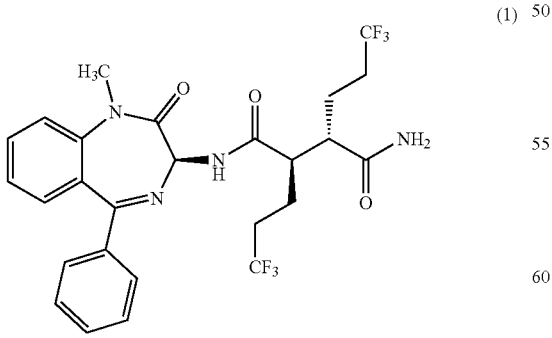

(1)

and/or at least one salt thereof in combination with a composition comprising a CDK 4 and 6 inhibitor, sorafenib, regorafenib, venetoclax, vorinostat, or a combination thereof.

2. The composition of claim 1, wherein said CDK 4 and 6 inhibitor comprises palbociclib, ribociclib, or abemaciclib, or a combination thereof.

3. A method of treating, suppressing or inhibiting adenoid cystic carcinoma (ACC) in a subject in need thereof comprising the step of administering to said subject a first composition comprising a compound represented by the structure of Compound (1):

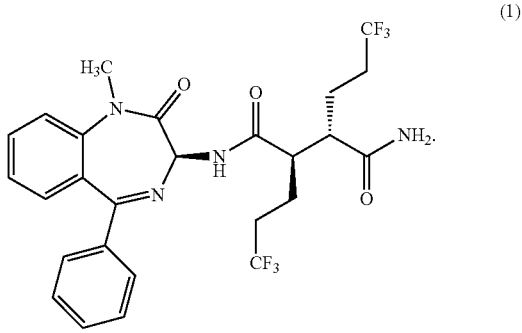 [SMILES: CN1C(=O)[C@@H](NC(=O)[C@H](CCC(F)(F)F)[C@H](CCC(F)(F)F)C(N)=O)N=C(c2ccccc2)c2ccccc21]

(1)

and/or at least one salt thereof, and a second composition comprising a CDK 4 and 6 inhibitor, sorafenib, regorafenib, venetoclax, vorinostat, or a combination thereof and wherein the subject has adenoid cystic carcinoma (ACC).

4. The method of claim 3, wherein said first composition and/or said second composition is intravenously administered to said subject.

5. The method of claim 3, wherein said first composition and/or said second composition is orally administered to said subject.

6. The method of claim 3, wherein said first composition and said second composition are administered together.

7. The method of claim 3, wherein said first composition and said second composition are administered at separate sites or at separate times.

8. The method of claim 7, wherein said first composition comprising Formula (I) is administered prior to and then again subsequent to the administration of said second composition.

9. The method of claim 3, wherein the adenoid cystic carcinoma (ACC) comprises a notch-activating mutation.

10. The method of claim 3, wherein said CDK 4 and 6 inhibitor comprises palbociclib, ribociclib, or abemaciclib, or a combination thereof.

* * * * *